(12) United States Patent
Cohen et al.

(10) Patent No.: US 9,283,154 B2
(45) Date of Patent: Mar. 15, 2016

(54) METHOD AND COMPOSITIONS FOR IMPROVING APPEARANCE OF SKIN

(71) Applicant: ELC Management LLC, Melville, NY (US)

(72) Inventors: Isaac David Cohen, Brooklyn, NY (US); Phillip Cummins, Livingston, NJ (US); Milan Franz Sojka, Coram, NY (US); David Walter Culhane, Commack, NY (US); Christina G. Fthenakis, Dix Hills, NY (US); Jennifer L. Sobel, Selden, NY (US); John Dudley Dreher, Sayville, NY (US); Yelena Mikhaylova, Smithtown, NY (US)

(73) Assignee: ELC Management LLC, New York, NY (US)

( * ) Notice: Subject to any disclaimer, the term of this patent is extended or adjusted under 35 U.S.C. 154(b) by 0 days.

(21) Appl. No.: 14/668,139

(22) Filed: Mar. 25, 2015

(65) Prior Publication Data

US 2015/0209244 A1    Jul. 30, 2015

Related U.S. Application Data

(62) Division of application No. 13/520,323, filed as application No. PCT/US2011/202048 on Jan. 5, 2011.

(60) Provisional application No. 61/357,809, filed on Jun. 23, 2010, provisional application No. 61/296,348, filed on Jan. 19, 2010.

(51) Int. Cl.
*A61K 8/02*    (2006.01)
*A61Q 1/02*    (2006.01)

(Continued)

(52) U.S. Cl.
CPC ............. *A61K 8/0283* (2013.01); *A61K 8/0241* (2013.01); *A61K 8/18* (2013.01); *A61K 8/19* (2013.01); *A61K 8/29* (2013.01); *A61K 8/8147* (2013.01); *A61K 8/8152* (2013.01); *A61Q 1/02* (2013.01); *A61Q 1/06* (2013.01); *A61Q 1/08* (2013.01); *A61Q 1/10* (2013.01); *D06P 5/04* (2013.01); *A61K 2800/262* (2013.01);

(Continued)

(58) Field of Classification Search
None
See application file for complete search history.

(56) References Cited

U.S. PATENT DOCUMENTS 3,215,724 A    11/1965    Strobel
3,439,088 A    4/1969    Edman et al.

(Continued)

FOREIGN PATENT DOCUMENTS

JP    61-18708 A    1/1986
JP    2001010929    1/2001

(Continued)

OTHER PUBLICATIONS

Encyclopdia Britannica, "Polymethyl methacrylate", retrieved from http://www.britannica.com/EBchecked/topic/1551203/polymethyl-methacrylate-PMMA on Apr. 28, 2015.*

(Continued)

*Primary Examiner* — Ernst V Arnold
*Assistant Examiner* — Jianfeng Song
(74) *Attorney, Agent, or Firm* — Julie Blackburn

(57) ABSTRACT

A method for making a composite particulate comprised of a colorant portion and a clear thermoplastic portion and cosmetic compositions containing the composite particulate.

10 Claims, 3 Drawing Sheets

Figure 1:
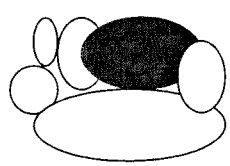
Figure 1:
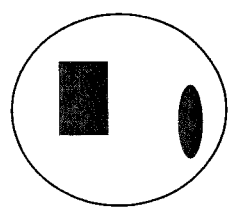
Figure 1:
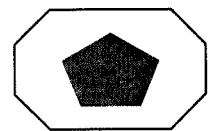
Figure 1:
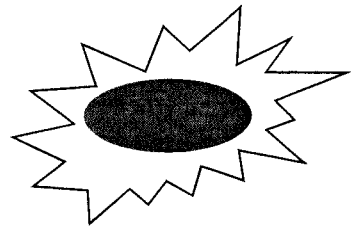

A.

C.

B.

D.

(51) Int. Cl.
*A61K 8/19* (2006.01)
*A61Q 1/08* (2006.01)
*A61Q 1/06* (2006.01)
*A61Q 1/10* (2006.01)
*D06P 5/04* (2006.01)
*A61K 8/81* (2006.01)
*A61K 8/18* (2006.01)
*A61K 8/29* (2006.01)

(52) U.S. Cl.
CPC ....... *A61K2800/31* (2013.01); *A61K 2800/412* (2013.01); *A61K 2800/43* (2013.01); *A61K 2800/651* (2013.01); *A61K 2800/654* (2013.01); *A61K 2800/805* (2013.01)

(56) References Cited

U.S. PATENT DOCUMENTS

| | | | |
|---|---|---|---|
| 3,781,417 A | 12/1973 | Welters et al. | |
| 3,818,105 A | 6/1974 | Coopersmith | |
| 4,089,800 A | 5/1978 | Temple | |
| 4,349,456 A | 9/1982 | Sowman | |
| 4,359,504 A | 11/1982 | Troy | |
| 4,590,235 A | 5/1986 | Troy | |
| 4,970,252 A | 11/1990 | Sakuta et al. | |
| 5,223,250 A | 6/1993 | Mitchell | |
| 5,236,986 A | 8/1993 | Sakuta | |
| 5,412,004 A | 5/1995 | Tachibana et al. | |
| 5,531,985 A | 7/1996 | Mitchell et al. | |
| 5,587,148 A | 12/1996 | Mitchell et al. | |
| 5,654,362 A | 8/1997 | Schulz et al. | |
| 5,733,531 A | 3/1998 | Mitchnick | |
| 5,760,116 A | 6/1998 | Kilgour et al. | |
| 5,811,487 A | 9/1998 | Schulz, Jr. et al. | |
| 5,837,793 A | 11/1998 | Harashima et al. | |
| 5,993,834 A | 11/1999 | Shah et al. | |
| 7,459,182 B2 | 12/2008 | Xiong et al. | |
| 2004/0105876 A1 | 6/2004 | Calello et al. | |
| 2005/0025730 A1 | 2/2005 | Chevalier et al. | |
| 2006/0034875 A1 | 2/2006 | Nakanishi et al. | |
| 2007/0009446 A1 | 1/2007 | Romero | |
| 2007/0071978 A1* | 3/2007 | Sojka et al. | 428/402.2 |
| 2007/0186814 A1 | 8/2007 | Schneider et al. | |
| 2008/0139453 A1 | 6/2008 | Yoshimi et al. | |
| 2009/0155371 A1 | 6/2009 | Sojka et al. | |
| 2009/0317430 A1 | 12/2009 | Cassin et al. | |
| 2009/0324659 A1 | 12/2009 | Polonka et al. | |
| 2010/0003293 A1 | 1/2010 | Elliott et al. | |

FOREIGN PATENT DOCUMENTS

| | | |
|---|---|---|
| JP | 2003-12461 A | 1/2003 |
| JP | 2004-323473 A | 11/2004 |
| JP | 2008-001678 A | 1/2008 |
| WO | 2004-024798 A1 | 3/2004 |
| WO | WO-2004/103335 | 12/2004 |
| WO | WO-2007/027503 | 3/2007 |

OTHER PUBLICATIONS

Refractive index database, "PMMA", retrieved from http://refractiveindex.info/?shelf=3d&book=plastics&page=pmma on Jun. 28, 2015.*

FDM Asia—Focus Magazine; Solid Wood & Panel Technology; Focus; Profile Wrapping: Performance Enhancement; http://www.fdmasia.com/index.php?mid=013&nid=326; Oct. 2007 (3 pages).

H.J. Vandenburg; A simple solvent selection method for accelerated solvent extraction of additives from polymers; The Analyst; vol. 124, 1999; 1707-1710.

ISR of PCT/US2011/020248 corresponding to the present application; Sep. 21, 2011.

S. Jones, et al.; The Development of Colour-Encapsulated Microspheres for Novel Colour Cosmetic; Journal of Microencapsulation, 2009, 26(4); 325-333; available online Oct. 20, 2008.

Written Opinion of PCT/US2011/020248 corresponding to the present application; Sep. 21, 2011.

Akzo Nobel Expancel 091 DE 40 d30 dry expanded microspheres: XP002735479; Retrieved from the Internet: URL:http://www.matweb.com/search/datasheet print.aspx?matguid=7581076dd4a7497c964c1035aa09714; Retrieved on Feb. 4, 2015.

Anonymous: "Leucophor BSB Liquid"; Clariant Textile Chemicals Directory of Chemicals; pp. 1-29; XP002735480; Retrieved from the Internat: URL:http://www.readbag.com/westco-spectra-brochure-wcp: Retrieved on Feb. 4, 2015: p. 19.

Anonymous: "What are Expancel Microspheres"; AkzoNobel; XP002735478; Retrieved from the Internet: URL:https://www.akzonobel.com/expancel/knowledge_center/tutorials/one/: retrieved on Feb. 4, 2015.

Rabe, Thomas et al.; "Encapsulated Organic Colorants to Mimic Naturally Flawless Skin";; Cosmeitcs & Toiletries; vol. 122, No. 6; Jun. 1, 2007; pp. 75-79; XP008174717; Wheaton, IL, US; ISSN: 0361-4387.

Stephen R. Jones, et al.: "The development of colour-encapsulated microspheres for novel colour cosmetics"; Journal of Microencapsulation; vol. 26, No. 4; Jun. 1, 2009; pp. 325-333; XP055166951; GB ISSN: 0265-2048; DOI: 10.1080/02652040802340706.

Supplemental European Search Report; EP11734985; Completion Date: Feb. 11, 2015; Mailing Date: Mar. 4, 2015.

* cited by examiner

A.

B.

C.

D.

METHOD AND COMPOSITIONS FOR IMPROVING APPEARANCE OF SKIN

CROSS-REFERENCE TO RELATED APPLICATIONS

This application is a divisional of U.S. Ser. No. 13/520,323 filed Feb. 6, 2013 which claims priority from PCT/US/2011/0202048 filed Jan. 5, 2011, which claims priority from Provisional Patent Application Ser. No. 61/296,348, filed Jan. 19, 2010 and 61/357,809 filed Jun. 23, 2010.

TECHNICAL FIELD

The invention is in the field of particulates and their use in cosmetic compositions with improved visual appearance on keratinous surfaces.

BACKGROUND OF THE INVENTION

A high percentage of women use foundation makeup. Current commercial products are of excellent quality and are available in shades that correctly match skin color. Yet foundation users remain unsatisfied. For example, a high percentage of ethnic women use foundation, yet are unhappy with the ashy, chalky tone that it often gives their skin. Often these products contain significant amounts of titanium dioxide which provides excellent coverage but can create a mask-like appearance. This is believed to be due in part to the undertones in skin color which provide the appearance of warmth or coolness in addition to depth and dimension. Foundation makeup that masks the natural undertones of skin often causes the facial skin to appear unnatural because it covers the natural dimensionality of the skin. The big need gap is for makeup products such as foundations that provide coverage without masking skin undertones, which provides an undesirable mask-like appearance.

Another reason for the importance of formulating such foundations has to do with SKU ("stock keeping unit") reduction. In order to meet the needs of all users, cosmetics companies must formulate a large number of foundation color choices to satisfy their customer base. Many of these shades sell very poorly or not at all. A large number of SKUs means larger cost to the cosmetics manufacturer. Thus, there is interest in formulating foundation makeup products that will match a wider range of skin colors. SKU reduction benefits both the cosmetics company and the consumer. In addition it removes some of the confusion associated with the consumer's color choices, which are never easy. Also more SKU's means increased product cost to the consumer because, ultimately, the higher cost of goods is reflected in a higher retail price to consumers.

It has been found that when color cosmetics are formulated with certain types of composite particulates that have a portion of clear or translucent thermoplastic material in the particulate, that color cosmetics will exhibit improved appearance on skin, including an improved appearance of dimensionality, depth and skin undertones, as well as reduction in the ashy, chalky, or mask-like appearance of color cosmetics such as foundation. In addition, the composite particulates facilitate reduction in the number of shades of the color cosmetic that are necessary to match all skin shades in a shade range.

It is the object of the invention to provide color cosmetic compositions that are more "universal", meaning that a particular color will match a larger number of color shades in a shade category. For example, a foundation that may be deemed more universal in its color matching properties may be designated Color #1 and it may match skin color shades 1, 2 and 3 in the shade category "Light" as opposed to the necessity of three different shades in the Light category with a traditional foundation.

It is a further object of the invention to provide a composite particulate containing a colorant portion and a clear or translucent thermoplastic portion.

It is a further object of the invention to provide a composition for application to keratinous surfaces such as skin, hair, or nails, comprising the composite particulate.

It is a further object to provide a method for improving the appearance of depth, dimensionality, and skin undertones by providing a natural appearance color cosmetic that contains composite particulates.

It is a further object of the invention to provide a method for reducing the ashy, chalky, or mask-like appearance of compositions such as foundation makeup on the skin by formulating the composition with composite particulates.

It is a further object of the invention to provide a method for reducing the number of SKUs in a color cosmetic shade range by formulating the color cosmetics with composite particulates.

SUMMARY OF THE INVENTION

The invention is directed to a composition for application to keratinous surfaces containing composite particulates in the fused agglomerate form having a portion comprised of at least one colorant and a portion comprised of at least one clear or translucent thermoplastic material, wherein the composite particulates contain, by weight of the total composite particulate, from about 1 to 99.9 parts of the colorant portion and from about 0.1 to 100 parts of the clear or translucent thermoplastic material portion, and wherein at least some of the composite particulates present in the composition have a colorant portion present.

The invention is further directed to a composite particulate in the fused agglomerate form having a portion comprised of at least one colorant and a portion comprised of at least one clear or translucent thermoplastic material, wherein the composite particulates contain, by weight of the total composite particulate, from about 1 to 99.9 parts of the colorant portion and from about 0.1 to 100 parts of the clear or translucent thermoplastic material portion, and wherein at least some of the thermoplastic material in the particulate is in the form of solid or hollow partial or complete spheres.

The invention is also directed to a method for imparting color to skin while improving the appearance of skin dimensionality, depth, or undertones by application of a composition comprising composite particulates having a portion comprised of at least one colorant and a portion comprised of at least one clear or translucent thermoplastic material.

A method for reducing the ashy, chalky, or mask-like effect of a color cosmetic composition on skin comprising substituting 0.1 to 99%, preferably 10-90% of the total colorant component present in the composition with composite particulates having a portion comprised of at least one colorant and a portion comprised of at least one clear or translucent thermoplastic material, wherein the composite particulates contain, by weight of the total composite particulate, from about 1 to 99.9 parts of the colorant portion and from about 0.1 to 100 parts of the clear or translucent thermoplastic material portion.

A method for reducing the number of SKUs in a shade range for a cosmetic product comprising providing a cosmetic product wherein from about 0.1-99%, preferably 10-90% by weight of the total colorant component comprises composite particulates.

DETAILED DESCRIPTION

I. Description of the Drawings

FIG. 1: Depicts types of composite particulates that may be used in the compositions and methods of the invention where the clear area within the black lines depicts the clear thermoplastic material portion of the composite particulate and the solid black portion depicts the colorant portion of the composite particulate.

1(A): is a composite particulate in the fused agglomerate form where the thermoplastic material is in the form of hollow or solid spheres, such that when such spheres are reacted with the solvent and colorant to form the composite particulate, at least some of the thermoplastic material portion remains in the form of entire or partial spheres.

1(B): is a composite particulate in the encapsulated form where the colorant portions are encapsulated within the thermoplastic material portion and where the composite particulate is generally spherical in shape.

1(C): is a composite particulate in encapsulated form having a non-spherical shape—depicted as substantially octagonal—and wherein the colorant portion is an irregular deposit embedded within the thermoplastic material portion.

1(D): is a composite particulate in the encapsulated form having a irregular shape and having the colorant portion encapsulated within.

Figure 2:
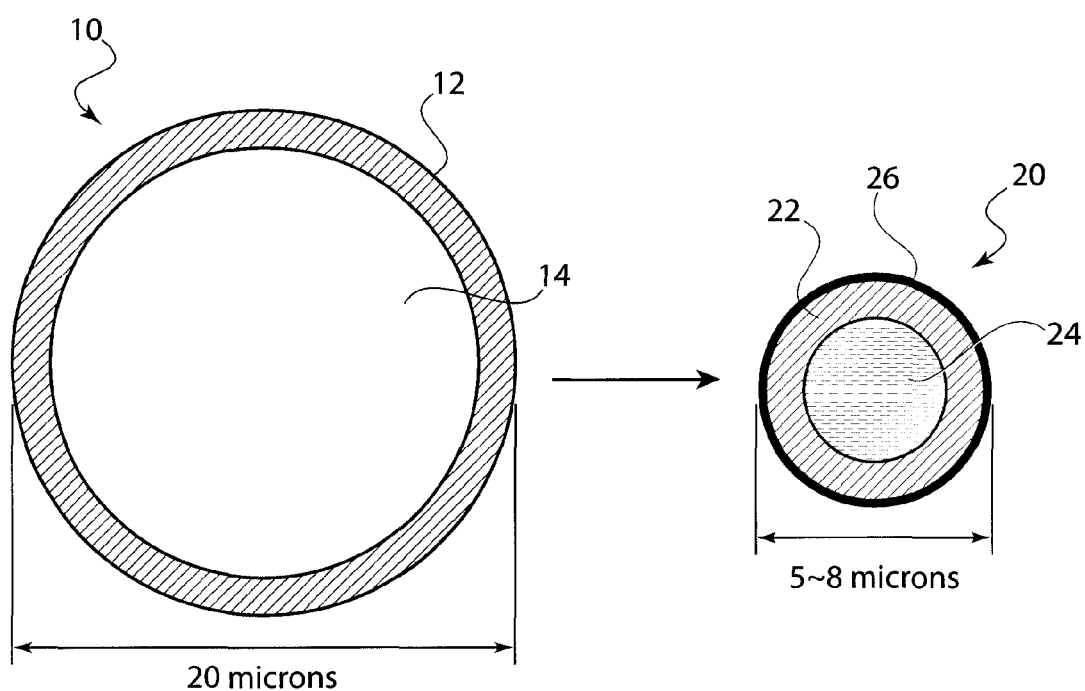

FIG. 2: Depicts a composite particulate in the form of a collapsed microsphere. The larger sphere depicts an untreated clear or translucent hollow microsphere with a deformable polymeric shell and an expandable fluid entrapped therein. The smaller sphere on the right depicts a collapsed polymeric shell with solid colorant particles trapped within and a liquid impermeable coating.

Figure 3:
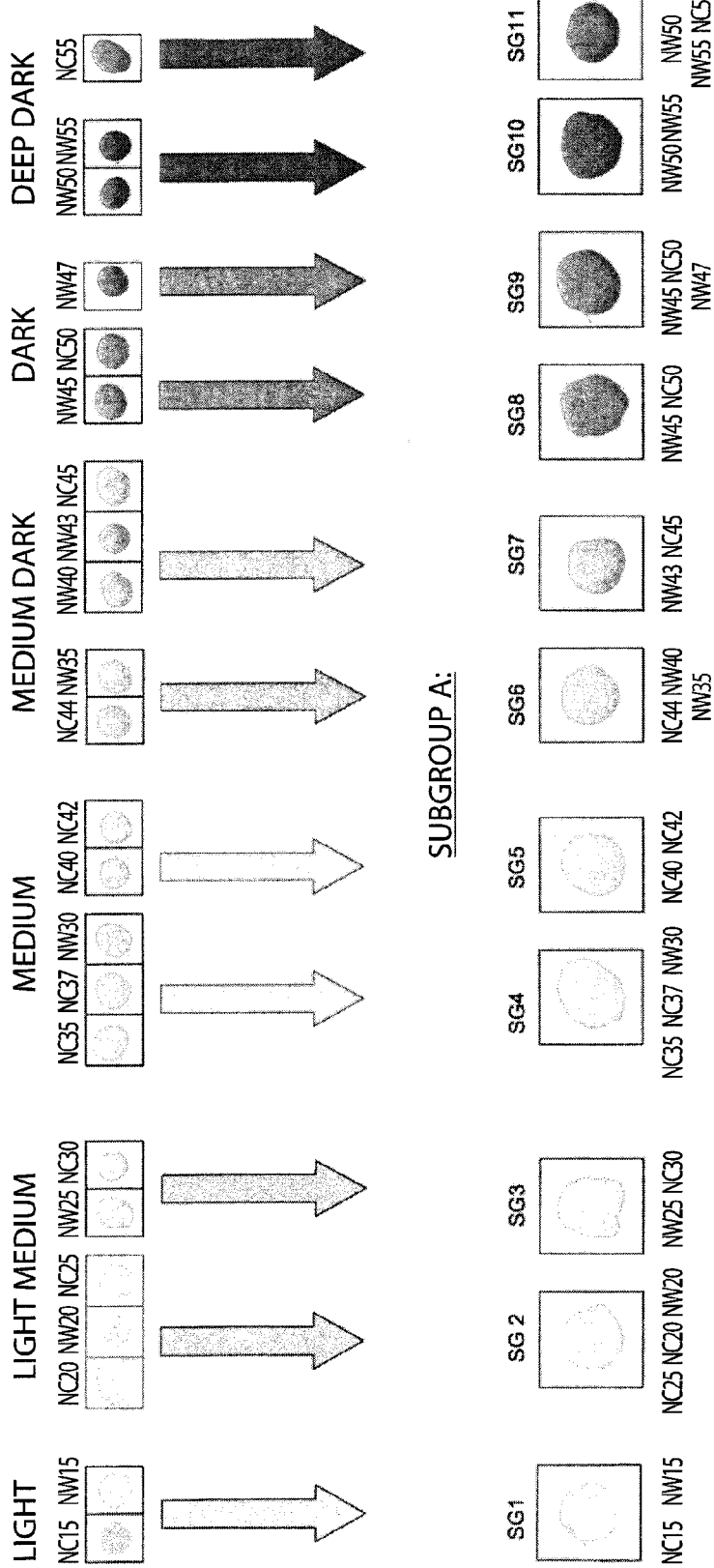

FIG. 3: is a chart that shows the reduction in foundation makeup color SKUs achieved with foundation formulas made with the composite particles of the invention (11 shades matched all skin colors) when compared with the shade palette of MAC Studio Fix Fluid SPF15 (19 shades necessary to match all skin colors). Thus, a 42% reduction (8 shades) in SKUs.

II. Definitions

In the terms used herein the singular shall include the plural and vice versa.

All percentages mentioned herein are percentages by weight unless otherwise indicated.

The term "agglomerate" means, when referred to the composite particulate, a cluster of colorants and the clear thermoplastic material where the clusters are fused, e.g. chemically or physically bonded together.

The term "ashy" or "chalky" means the whitish, ash-like appearance that cosmetics such as foundation may exhibit on skins, particularly darker skins.

The term "clear" means the same as "transparent" and that the thermoplastic material permits both the passage of light and is sufficiently free of cloudiness or haziness to provide a clear view of what lies behind. In some cases the thermoplastic materials used in the compositions and methods of the invention may be individually be in the clear particulate or spherical particulate form, yet when viewed in bulk they may exhibit a whitish or grayish powder appearance. In this case it is the appearance of the individual particulate that governs.

The term "collapsed microsphere" means an originally hollow microsphere that, during the manufacturing process, has formed channels and interstices into which colorants are entrapped within and dispersed throughout. Each individual microsphere with the dispersed and trapped colorants forms its own closed system. In contrast, in fused agglomerates the colorant deposit is found in agglomerates that are fused with agglomerates formed from the clear thermoplastic material.

The term "colorant" when used herein means colored pigments, or non-colored or white particulates that are sometimes used as fillers or to mute color in cosmetic compositions. In general the term "colorant" excludes clear or translucent thermoplastic materials in the form of particulates.

The term "colorant component" means the total amount of the colorants as described in section II below that are present in the composition.

The term "composite particulate" means a solid particle that contains a portion comprised of at least one colorant and a portion comprised of at least one clear or translucent thermoplastic material wherein the two portions are fused together, e.g. not present as a simple unreacted mixture.

The term "encapsulated particulate" means a type of composite particulate where the colorant component is encapsulated within the clear thermoplastic material.

The term "fused agglomerate" means with respect to the composite particulate, that it is an agglomeration of colorant and clear or translucent thermoplastic material where the agglomerates are fused, e.g. chemically bound, to each other. In the case where the clear thermoplastic portion of the fused agglomerate is in the form of hollow or solid spherical particles, the fused agglomerate may contain a thermoplastic portion comprising agglomerated partial or entire solid or hollow spheres.

The term "mask-like" means the appearance of a color cosmetic composition such as foundation on the facial skin when the composition masks skin undertones to a degree sufficient to provide a visually unnatural appearance.

The term "room temperature" means a temperature of about 25° C.

The term "SKU" means stock keeping unit, which is the lowest level of product detail. SKU numbers are generally in the format xxxx-xx where the first four numbers designate the product name and, for color cosmetics, the last two numbers the shade code. For example a SKU number of 1234-56 means, for example, that foundation makeup product line "x" is designated by the number 1234, and the numbers "56" refer to one particular shade of the foundation makeup.

The term "translucent" means, with respect to the thermoplastic material, that it permits passage of light but has sufficient cloudiness or haziness to prevent a clear view of what lies behind. In cases where the thermoplastic material is in the individual particulate form the particles may be translucent, but when viewed in the bulk form such translucent particles may appear as a whitish or grayish powder. In this case it is the appearance of the individual particles that governs.

II. The Composite Particulate

A. Description

The composite particulate may be in the form of an agglomerate, preferably a fused agglomerate, a collapsed microsphere, or an encapsulated particulate.

When the composite particulate is in the form of a fused agglomerate, it is generally made by blending a mixture of one or more colorants and one or more clear or translucent thermoplastic synthetic or natural polymeric materials to create a composite that retains properties of both the colorant and the thermoplastic material. Preferably the colorants and the clear or translucent thermoplastic material used to make the composite particulate are in particulate form.

The composite particulate is solid at room temperature and has a particle size ranging from about 0.01 to 200, preferably from about 0.1 to 150, more preferably from about 1 to 100 microns in diameter. The composite particulate may have a variety of shapes including spherical or other types of irregular shapes. The composite particulate preferably contains a colorant portion ranging from about 0.1 to 99%, preferably from about 0.5 to 90%, more preferably from about 5-80%; and clear or translucent thermoplastic portion ranging from about 0.1 to 100%, preferably from about 0.5 to 90%, more preferably from about 5 to 80%, all percentages by weight of the total composite particulate.

B. Components of the Composite Particulate

1. Colorants

Colorants suitable for use in making the composite particulate include organic pigments, which are generally referred to as D&C and FD&C colors such as blues, browns, greens, oranges, reds, yellows, etc. Such organic pigments may also include insoluble metallic salts of certified color additives, referred to as D&C Lakes or FD&C Lakes.

Suitable colorants also include inorganic pigments such as iron oxides, ultramarines, chromium, chromium hydroxide colors, and mixtures thereof. Iron oxides of red, blue, yellow, brown, black, and mixtures thereof are suitable.

Further examples of suitable colorants include colored or non-colored (for example white) non-pigmented powders. Examples include non-clear or translucent particulates such as bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof.

Preferred colorants have a particle size ranging from about 0.001 to 150 microns, preferably from about 0.005 to 100 microns, more preferably from about 0.1 to 50 microns.

2. Clear or Translucent Thermoplastic Material

The clear or translucent thermoplastic material is preferably a synthetic polymer. Generally, in order to provide the desired clarity or translucence the index of refraction of the polymer material used to prepare the composite ranges from about 1.3 to 1.8, or 1.4 to 1.6. In addition, the clear or translucent polymer is generally a solid at room temperature, and may have a density ranging from about 0.5 to 5 grams/cm$^3$. The polymer preferably has a melting point ranging from about 50° to 200° C.

The material used to prepare the composite may be in the form of hollow or solid spheres. Or it may be in the form of a solid block or film which may be ground to form particulates of varying sizes and shapes. In one preferred embodiment of the invention the clear or translucent thermoplastic material is in the form of particulates, which may be hollow or solid spherical particulates; preferably having particle size ranging from about 0.01 to 150 microns, more preferably from 0.1 to 100 microns, even more preferably from 0.5 to 75 microns.

Suitable polymers for making the clear or translucent thermoplastic material used in the manufacture of the composite particulate include, but are not limited to those set forth herein.

(a). Homo- or Copolymers of Ethylenically Unsaturated Monomers (i). Acrylic Acid, Methacrylic Acid or Their Simple Esters Suitable polymers include homo- or copolymers from ethylenically unsaturated monomers such as acrylic acid, methacrylic acid, or their simple $C_{1-20}$ aliphatic or aromatic esters. Examples of such monomers include methyl acrylate, methyl methacrylate, acrylate, ethyl acrylate, ethyl methacrylate, butyl acrylate, butyl methacrylate, hexyl acrylate, hexyl methacrylate, and so on.

It is possible for the polymer to be uncrosslinked or partially crosslinked. If crosslinked, divinyl crosslinking agents in the form of alpha omega dienes may be suitable, for example those having 2 to 10 carbon atoms. Examples include ethene, propylene, butene and so on. If the polymer is crosslinked it is believed that when it is contacted with the solvent the polymer will tend to swell rather than completely solvate. If the polymer was in the form of spherical particulates, this will result in a final composite particle where the thermoplastic portion that is present may contain either partial or complete spheres. It is believed that when the composite particulate contains sphere portions this contributes to the unique visual effect provided by the composite particulate.

One preferred polymer is polymethylmethacrylate (PMMA) in spherical form having a specific gravity ranging from about 1.100 to 1.250 gm/ml, a particle size ranging from about 4.5 to 8.5 microns, and density ranging from 1 to 1.5 gm/cm$^3$. Such a particle may be purchased from SEPPIC Corporation under the trade name Sepimat P or from Tomen American under the trade mark Microsphere M-100.

Other types include styrenated acrylates (copolymers of styrene and acrylic acid, methacrylic acid or their simple C1-10 esters); styrene acrylonitrile ("SAN") polymers, acrylonitrile butadiene styrene copolymers ("ABS").

(ii). Homo- or Copolymers of Alkenes

Also suitable are homo- or copolymers of C2-10 alkenes such as polyethylene, polypropylene, polybutene, and the like which may also be crosslinked. One suitable alkene is an uncrosslinked ethylene homopolymer sold under the trade name Performalene 400® which is a high molecular weight polyethylene homopolymer sold by Baker Hughes.

(b). Polycarbonates

Also suitable as thermoplastic material used to make the composite are various types of polycarbonates. The term "polycarbonate" means polymers having functional groups linked together by carbonate (—O—C(O)—O—) groups, and they may be polyaromatic carbonates or polyaliphatic carbonates. The polycarbonates may be in the form of solid or hollow spherical particles, ground particulates, or in a film or block form.

3. Solvents

Suitable solvents for swelling or solvating the clear or translucent thermoplastic material can be determined by ascertaining their Hildebrand Solubility Parameter which is the square root of the cohesive energy density of the solvent. The formula for the Hildebrand Solubility Parameter (δ) is:

$$\delta = \sqrt{(Hv-RT)/Vm}$$

expressed in (calories/cm$^3$)$^{1/2}$ wherein: $H_v$=the heat of vaporization
R=the gas constant
T=temperature
$V_m$=molar volume.

One type of solvent suitable for use in preparing the composite particulate may be identified by its Hildebrand Solubility Parameter. In this case, solvents having a Hildebrand Solubility Parameter ranging from about 1 to 16, more particularly 3-15, more preferably 5-10 (calories/cm$^3$)$^{1/2}$ may be good solvents for use in preparing the composite particulate.

Identification of suitable solvents for the thermoplastic materials selected may also be determined by the procedures set forth in "A Simple Solvent Selection Method for Accelerated Solvent Extraction of Additives from Polymers", *Analyst*, Volume 124, pages 1707-1710—The Royal Society of Chemistry, 1999, hereby incorporated by reference in its entirety.

Other types of preferred solvents include aliphatic, aromatic, or heterocyclic, saturated or unsaturated hydrocarbon chains ranging from about 1 to 12, preferably from about 1 to 10 carbon atoms, more preferably from about 2 to 8 carbons. Such carbon chains may have one or more carbonyl, hydroxyl, amine, halogen, ether linkages, or amide groups substituted on the hydrocarbon chain. Examples of such solvents include acetone, xylene, methylethyl ketone (MEK), dimethylformamide, dimethylchloride, trichloroethylene, trichloromethane, methanol, ethanol, isopropanol, ethyl acetate, butyl acetate, toluene, benzene, cyclohexane, amyl acetate, carbon tetrachloride, toluene, tetrahydrofuran, benzene, diacetone alcohol, ethylene dichloride, methylene chloride, DMSO, morpholine, cellosolve, pyridine, propanol; or $C_{1-4}$ mono- or dialkyl ethers of ethylene glycol, and the like. Most preferred are ethanol, acetone, xylene, or MEK. Most preferred is acetone.

C. How to Make

The composite particulate in the fused agglomerate form may be made by combining the thermoplastic material and colorant then mixing with an amount of solvent sufficient to cause the thermoplastic material to swell (e.g. expand) or solvate. The ratio of thermoplastic material to colorant to solvent may be determined by ascertaining the particular thermoplastic material, the amount in which it is present, and what solvent would be most appropriate for swelling or solvating the thermoplastic material. Generally, suitable ratios of colorant to thermoplastic material to solvent may range from about 0.1-50 parts colorant to 0.1 to 100 parts thermoplastic material to 0.1 to 100 parts solvent. Preferably the process is conducted at room temperature, although, if desired, heat may be applied. The colorant, solvent, and thermoplastic material are combined for a time sufficient to permit the solvent to swell or solvate the thermoplastic material. The amount of time may range from 1 to 72 hours, or from 10 to 50 hours. After the appropriate time period the mixture is removed from the vessel and spread into a glass baking dish to form a flat surface, then allowed to dry for 12 to 72 hours, preferably from 24 to 48 hours, or until hardened. The hardened mixture is then removed from the dish and broken up with the hands into smaller pieces. The resulting pieces are subjected to various procedures such as milling and sieving to achieve composite particulates having the desired shape and size.

The colorant portion and thermoplastic material portion of the composite particulate are fused such that the entire composite is in a particulate form. In the preferred embodiment the composite particulate may appear as a fused agglomerate of the colorant component and the thermoplastic material component, and wherein the latter will exhibit portions that are in the solid or hollow partial spherical form; that is spheres that were swelled but not completely solvated in the manufacturing process.

If desired the composite particulates may be coated with various materials to make them more hydrophilic or lipophilic as desired. Suitable coatings include, but are not limited to oils, structuring agents, and any one or more of the ingredients further listed herein as being suitable for use in cosmetic compositions of the invention. Further examples include silicone elastomers, silicone resins, silicone gums, synthetic or natural waxes, and the like. If the composite particulates are coated, the coating comprises, preferably, from about 0.1 to 45%, more preferably from about 0.1 to 30%, most preferably from about 1 to 10% by weight of total composite particulate. One particularly preferred coating is trisiloxane/dimethicone silylate.

D. Another Embodiment of the Composite Particle

Also suitable is a composite particle in the collapsed microsphere form. Such particulates are disclosed in U.S. Patent Publication No. 2009/0155371, hereby incorporated by reference in its entirety. In this case the clear or translucent thermoplastic material is in the form of a collapsed microsphere having the colorant entrapped entirely within the microsphere rather than forming a portion of an agglomerate. The collapsed microsphere may be optionally coated with a membrane or coating in the same manner as set forth with the fused agglomerate form of the composite particulate. These composite particles in the form of collapsed microspheres may be formed by:

(a) forming a gelled mixture by mixing either simultaneously or sequentially in any order: (1) clear or translucent hollow microspheres having internal channels, preferably in the open cell form, that have a deformable polymeric shell having entrapped therein an expandable fluid, (2) a polar organic solvent capable of swelling but not dissolving the polymeric shells of the hollow microspheres, and (3) colorants, wherein micro-channels are formed in the swelled polymer shells to allow entry of the colorants into the hollow microspheres and exit of the expandable fluid therefrom, thereby forming micro spheres that each comprises a collapsed polymeric shell in a gelled state and has one or more of said colorants entrapped therein;

(b) removing the expandable fluid and the polar organic solvent from the gelled mixture; and (c) coating the microspheres with a film-forming material to form a liquid-impermeable coating thereon.

In the resulting collapsed microspheres the colorant particles are entrapped within the microspheres. In some cases the colorant that is used may be in the form of submicron particle sizes, in which case the collapsed microspheres may have an average particle size that may be at least 10 times, preferably 20 times, more preferably 50 times, and most preferably 100 times, larger than the average particle size of the colorant particles used to make the composite particulate.

Entrapment of the pigment particles is achieved in the present invention by first providing clear or translucent hollow microsphere that have a deformable polymeric shell and which may or may not have an expandable fluid within the hollow portion of the microsphere. The microspheres are then mixed with, either sequentially in any order or simultaneously, a polar organic solvent capable of swelling but not dissolving the polymeric shells of the hollow microspheres and solid particles to be entrapped. A gelled mixture is thereby formed, which contains micro spheres with polymeric shells in a gelled state, which are sufficiently swelled so as to have micro-channels or through-holes formed therein to allow entry of the colorant particles into the microspheres. Such micro-channels or through-holes in the swelled polymeric shells of the microspheres also allow exit of the expandable fluid from the microspheres, thereby causing immediate collapse or implosion of the polymeric shells and entrapping the colorant particles inside the microspheres. Subsequently, the expandable fluid and the polar organic solvent are removed from the gelled mixture. Preferably but not necessarily, a film-forming material is coated over the collapsed polymeric shells to form a liquid-impermeable membrane thereon, which functions to isolate the collapsed polymeric shells of the microspheres from any solvent in the surrounding environment that may swell or otherwise affect the structural integrity of such polymeric shells. In this manner, the solid particles can be securely entrapped inside the microspheres with little or no risk of leaking out.

The hollow microspheres used as the clear or translucent thermoplastic material, as initially provided (i.e., before mixing with the solid particles and the polar organic solvent) are preferably expandable hollow polymeric microspheres, each of which contains a deformable polymeric shell that is gas-tight and has enclosed or encapsulated therein an expandable fluid. Upon heating, the enclosed or encapsulated fluid can expand volumetrically to apply pressure on the interior wall of the deformable polymeric shell. At the same time, the elevated temperature may cause the polymeric shell to soften, thereby allowing the entire microsphere to expand in a manner similar to a balloon.

The deformable polymeric shells of the hollow microspheres can be formed of any synthetic or natural crosslinked or un-crosslinked polymer. If the polymer is crosslinked, it is preferred that it is weakly crosslinked. Preferably, but not necessarily, the polymeric shells of the hollow microspheres comprise at least one synthetic polymer obtained by polymerization of one or more ethylenically unsaturated monomers to form homopolymers or copolymers of ethylenically unsaturated monomers or copolymers of ethylenically unsaturated monomers and one or more organic groups. Examples of ethylenically unsaturated monomers that may be suitable include, for example, vinylidene chloride, vinyl chloride, acrylonitrile, acrylic acid and its corresponding $C_1$-$C_{20}$ aliphatic or aromatic esters, methacrylic acid and its corresponding $C_1$-$C_{20}$ aliphatic or aromatic esters, acrylamide, methacrylamide, vinyl pyrrolidone, alkenes such as styrene, ethylene, propylene, butylene, methylpentene, 1,3-butadiene, and the like. The polymeric shells of the hollow microspheres may also be formed of suitable synthetic polymers, such as polyesters, polyamides, polyphthalamides, polyimides, polycarbonates, polyketones, cellulose acetate, polysulfones, polyphenylene sulfides, polyphenylene oxides, polylactic acids, polyvinylpyrrolidone, polystyrene, polyacrylonitrile, polyacrylamide, polyacrylates, and copolymers of the above-listed polymers. In a particularly preferred embodiment, the deformable polymeric shells of the hollow microspheres are formed of a copolymer of vinylidene chloride, acrylonitrile, and/or methyl methyacrylate.

The expandable fluid inside the hollow microspheres of the present invention can be any suitable gas (e.g., air or nitrogen) or volatile liquid hydrocarbons (e.g., isobutane or isopentane). Preferably, the expandable fluid is selected from the group consisting of air, nitrogen, isobutane, and isopentane. More preferably, the expandable fluid is either isobutane or isopentane.

Hollow microspheres having deformable polymeric shells comprised of a copolymer of vinylidene chloride, acrylonitrile, and methylmethacrylate with an expandable fluid comprised of isobutane or isopentane are commercially available under the trade name of EXPANCEL® from Expancel, Inc. at Duluth, Ga. The EXPANCEL® hollow microspheres are available in various forms, e.g., dry, wet, unexpanded or pre-expanded. Both the dry, unexpanded microspheres (EXPANCEL® DU) and the dry, expanded microspheres (EXPANCEL® DE) can be used in the present invention for entrapping and stabilizing the solid particles. The EXPANCEL® DU microspheres have an average particle size ranging from about 6 to about 40 microns and a density of about 1-1.3 $g/cm^3$. The EXPANCEL® DE microspheres have an average particle size ranging from about 20 to about 150 microns and a density of about 0.03-0.07 $g/cm^3$.

Suitable solvents for making a composite particulate in the form of collapsed microspheres having colorants dispersed therein are those as set forth with respect to the fused agglomerated composite particulate as described above, and in the same general amounts.

Upon mixing with untreated hollow microspheres, the polar organic solvent can swell the polymeric shells of the hollow microspheres significantly and thereby convert the gas-tight polymeric shells of the untreated hollow microspheres into a gelled state with multiple micro-channels or pores formed therein.

The colorants used in formation of the collapsed microsphere are the same as those set forth with respect to the fused agglomerate and in the same general amounts.

It is possible to incorporate two or more different types of colorants into the microsphere to create unique visual effects. In one specific embodiment of the composite particulate, two or more different types of pigment particles are incorporated into the microspheres.

It is preferred that where the composite particulate is in the form of collapsed microspheres, that the average particle size of the colorants used should be significantly smaller than that of the hollow microspheres so that the colorants can readily enter and be entrapped by the hollow microspheres that forms the clear thermoplastic material. Preferably, the average size of the colorant particles is less than about 1 micron, more preferably from about 0.001 micron to about 0.1 micron, and most preferably from about 0.01 to about 0.05 micron.

The hollow microspheres, the solvent and the colorant as described herein are mixed together, either simultaneously or sequentially, to form a gelled mixture. If mixed sequentially, the ingredients can be added and mixed in any suitable order. For example, the hollow microspheres and the colorant can be blended together first, followed by addition of the solvent to form a slurry. For another example, the colorant can be dispensed in the solvent first, and then mixed with the hollow microspheres. For still another example, the hollow microspheres can be added to the organic solvent to form a gel first, and the colorants are then added into the gel. In any event, all the ingredients are well mixed until a homogenous mixture is formed. The weight ratio between the hollow microspheres and the polar organic solvent is preferably from about 1:3 to about 1:100 and more preferably from about 1:20 to about 1:50, so that the polymeric shells of the hollow microspheres can be sufficiently swelled by the solvent. The weight ratio between the colorants and the hollow microspheres can range widely from about 1:10 to about 100:1, preferably from about 2:3 to about 10:1, and more preferably from about 1:1 to about 2:1.

Because the polymeric shells of hollow micro spheres are comprised of a non-crosslinked or weakly crosslinked polymer the solvent molecules, which are sufficiently small in comparison with the polymeric molecules, can enter between the polymeric chains, interrupt the intermolecular bonds between neighboring polymeric chains, and pull the polymeric chains apart from each other. Consequently, the polymeric shells of the hollow microspheres are swelled by the polar organic solvent, so as to form a gelled mixture that contains porous networks of interconnected polymeric chains spanning or dispersed throughout the volume of the solvent. The polymeric shells of the microspheres in such a gelled state are no longer gas-tight, but have become porous, i.e., with sufficiently large micro-channels therein to allow entry of the colorant into the sufficiently swelled microspheres. At the same time, the expandable fluid exit from such microspheres through the micro-channels, causing the gelled polymeric shells to collapse or implode and resulting in shrunken microspheres with significantly decreased overall volume. In this manner, the colorants become entrapped within the collapsed polymeric shells of the shrunk microspheres.

Such shrunken microspheres may have an average particle size ranging from about 1 to 15 microns, and more from about 5 microns to about 8 microns. The shrunk microspheres are significantly smaller in size than the untreated hollow microspheres. Further, the shrunken microspheres are no longer hollow, but are now filled by the pigment particles with little or no empty space left therein. At the same time, the polymeric shells of the microspheres remain in a gelled state, i.e., swelled by the polar organic solvent. It is important to note that the shrunken microspheres of the present invention, although morphologically and volumetrically modified by the gelling process, remain as separate particles in the gelled mixture with little or no coalescence. Subsequent drying of the gelled mixture therefore forms fine free-flowing powders, which contain microspheres with well-defined surface boundaries and minimum clumping or agglomeration.

The gelling process as described herein is fundamentally different from the well known sol gel process. In a typical sol-gel process, metal alkoxide and metal chloride precursors are first solubilized to form a solution (sol) and then undergo hydrolysis and polycondensation reactions to form a colloid system composed of solid particles dispersed in a solvent, followed by evolvement toward the formation of an inorganic network containing a liquid phase (gel), which can be dried to remove the liquid phase from the gel thus forming a porous material. In contrast, the gelling process of the present invention does not involve hydrolysis or polycondensation reactions, and it forms a network of water-insoluble polymeric chains dispersed in the polar organic solvent.

The gelled mixture as described hereinabove can be subjected to de-gassing, in which the gelled mixture is placed under a reduced pressure or vacuum conditions, so as to remove the expandable fluid from the gelled mixture. Subsequently, a second solvent that is miscible with the polar organic solvent previously used for swelling/gelling the microspheres can be added into the de-gassed gelled mixture with sufficient agitation, so as to "quench" the gelled mixture by separating the swelled microspheres from one another. For example, when the polar organic solvent is acetone, the second solvent can be water, which is miscible with acetone. Due to the immiscibility between the polar organic solvent and the second solvent, the microspheres become more spatially separated from one another and therefore more dispersed. Such further dispersion of the microspheres functions to minimize the risk of coalescence during subsequent drying of the gelled mixture. Further separation of the microspheres can be achieved by a filtration or centrifugation step, which is optional for the purpose of the present invention.

After the de-gassing and quenching steps, both the polar organic solvent and the second solvent are preferably removed from the gelled mixture to form dry, free-flowing powders containing the microspheres with the solid particles entrapped therein. Removal of the polar organic solvent and the second solvent can be readily achieved by various separation and/or drying techniques well known in the art, such as decantation, centrifugation, filtration, solvent extraction, air drying, vacuum drying, freeze drying, spray drying, fluid bed drying, supercritical fluid drying, and the like. The polymeric shells, which have been previously swelled by the polar organic solvent and become porous with micro-channels extending there through, shrink significantly and lose their porosity after being dried. In other words, the micro-channels formed through the swelled polymeric shells of the microspheres during the gelling step close up after the drying step, thereby securely entrapping the pigment particles inside the micro spheres. To minimize agglomeration between the dried micro spheres, the resulting powders can be further subject to milling and sieving through one or more screens.

In order to eliminate or minimize the potential risk of the entrapped pigment particles leaking out of the dried microspheres, the resulting composite particulate can be coated or otherwise surface-treated. Suitable coating ingredients include those set forth herein, such as silicones, waxes, oils, and the like as described with respect to ingredients suitable for use in the compositions of the invention. Where the composite particulate is in the form of a collapsed microsphere, it is preferred that the coating be impermeable to liquid to prevent any liquid from entering into the microsphere and causing the colorants present to leak out.

The resulting composite particulates may have an average particle size ranging from about 1 to about 50 microns, more preferably from about 1 to about 15 microns, and most preferably from about 5 to about 8 microns, as determined by a Malvern Particle Size Analyzer, available from Malvern Instrument at Worcestershire, UK. The entrapped colorants may comprise from about 10% to about 90% of the total weight of the total composite particulate, 30% to about 75% of the total weight, and most preferably from about 40% to about 60% of the total weight.

FIG. 2 depicts the schematic views of an untreated hollow microsphere 10 and a microsphere 20 according to one embodiment of the present invention, which is formed by processing the untreated hollow microsphere 10 according to the method described hereinabove. Specifically, the untreated hollow microsphere 10 includes a gas-tight and deformable polymeric shell 12 with an expandable fluid 14 entrapped therein. The diameter of the untreated hollow microsphere 10 is approximately 20 microns. In contrast, the microsphere 20 of the present invention includes a collapsed polymeric shell 22 with pigment particles 24 entrapped therein and a liquid-impermeable membrane 24 coated over. The diameter of the microsphere 20 is significantly smaller than that of the untreated hollow microsphere 10 and approximately ranges from about 5 to about 8 microns.

Also suitable are composite particulates in the form of encapsulated colorants such as those that are disclosed in U.S. Pat. Nos. 5,223,250; 5,531,985; 5,587,148; and 5,733,531, all of which are hereby incorporated by reference in their entirety.

III. The Cosmetic Compositions

The composite particulates may be used to prepare a variety of compositions suitable for application to keratinous surfaces, including but not limited to creams, lotions, sunscreens, foundation makeup, concealer, eyeshadow, blush, eyeliner, mascara, lipstick, lip gloss, nail enamel, hair products such as shampoo, conditioner, styling products; and so on. The compositions may be in the form of aqueous gels or dispersions, emulsions, or anhydrous compositions, and in the liquid, semi-solid or solid form. Suitable aqueous gels contain from about 0.1 to 99% water from about 1-99.9% of other cosmetic ingredients. Emulsions may be in the oil in water or water in oil form, and generally comprise from about 0.1 to 99% water and from about 0.1 to 99% oil. Anhydrous compositions generally contain less than about 1% water, in addition to 0.1 to 90% oils, and optionally other ingredients. Such compositions may contain one or more of the following ingredients.

In general, compositions where the total colorant component comprises from about 30-70 parts, preferably 40-60, most preferably about 50 parts of iron oxide to about 70-30, preferably 60-40, most preferably about 50 parts of thermoplastic material provide a desirable color effect that results in a natural coverage look. Expressed in a different way, the advantageous color effect can be achieved with a combination of about 50-80 parts composite particulate, more particularly about ⅔ composite particulate and about 20-50, more specifically about ⅓ parts iron oxide.

A. Oils

Suitable oils include silicones, esters, vegetable oils, synthetic oils, including but not limited to those set forth herein. Suggested amounts are from about 0.1 to 99%, preferably from about 0.5 to 95%, more preferably from about 1 to 80%. The oils may be volatile or nonvolatile, and are preferably in the form of a pourable liquid at room temperature. The term "volatile" means that the oil has a measurable vapor pressure, or a vapor pressure of at least about 2 mm of mercury at 20° C. The term "nonvolatile" means that the oil has a vapor pressure of less than about 2 mm of mercury at 20° C.

1. Volatile Oils

Suitable volatile oils generally have a viscosity ranging from about 0.5 to 5 centistokes 25° C. and include linear or cyclic silicones, paraffinic hydrocarbons, or mixtures thereof.

(a). Volatile Silicones

Cyclic silicones are one type of volatile silicone that may be used in the composition, including those having the following formula:

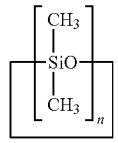

where n=3-6, preferably 4, 5, or 6.

Also suitable are linear volatile silicones, for example, those having the general formula:

where n=0, 1, 2, 3, 4, or 5, preferably 0, 1, 2, 3, or 4.

Cyclic and linear volatile silicones are available from various commercial sources including Dow Corning Corporation and General Electric. The Dow Corning linear volatile silicones are sold under the tradenames Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone, ethyl trimethicone, propyl trimethicone, butyl trimethicone and the like. Methyl trimethicone may be purchased from Shin-Etsu Silicones and has the trade name TMF 1.5, having the viscosity of 1.5 centistokes at 25° C. Such silicones have the general formula:

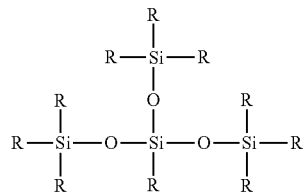

wherein each R is independently a $C_{1-4}$ alkyl, preferably methyl.

(b). Volatile Paraffinic Hydrocarbons

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference.

Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

2. Non-volatile Oils

A variety of nonvolatile oils are also suitable for use in the compositions of the invention. The nonvolatile oils generally have a viscosity of greater than about 5 to 10 centistokes at 25° C., and may range in viscosity up to about 1,000,000 centistokes at 25° C. Examples of nonvolatile oils include, but are not limited to:

1. Esters

Suitable esters are mono-, di-, and triesters. The composition may comprise one or more esters selected from the group, or mixtures thereof.

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on.

Suitable diesters are the reaction product of a dicarboxylic acid and an aliphatic or aromatic alcohol, or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e.

contains 12-22 carbon atoms. The dicarboxylic acid may also be an alpha hydroxy acid. The ester may also be in the dimer or trimer form. Examples of diester oils that may be used in the compositions of the invention include those having a lower viscosity, e.g. diisostearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

Suitable triesters comprise the reaction product of a tricarboxylic acid and an aliphatic or aromatic alcohol, or alternatively, the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters", the text of which is hereby incorporated by reference in its entirety.

2. Hydrocarbon Oils

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

3. Glyceryl Esters of Fatty Acids

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diisostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

4. Nonvolatile Silicones

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone.

For example, such nonvolatile silicones may have the following general formula:

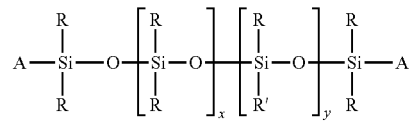

wherein R and R' are each independently $C_{1-30}$ straight or branched chain, saturated or unsaturated alkyl, phenyl or aryl, trialkylsiloxy, and x and y are each independently 1-1,000,000; with the proviso that there is at least one of either x or y, and A is alkyl siloxy endcap unit.

Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the trade names Abil Wax 9801, or 9814.

B. Humectants

The compositions of the invention may also contain one or more humectants. If present, suggested ranges are from about 0.001 to 50%, preferably from about 0.01 to 45%, more preferably from about 0.05 to 40% by weight of the total composition. Examples of suitable humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, trehalose, and so on. Also suitable is urea or sugar derivatives, e.g. ethylhexylglycerin. In one preferred embodiment, the humectants used in the composition of the invention are $C_{1-6}$, preferably $C_{2-4}$ alkylene glycols, most particularly butylene glycol.

C. Surfactants

If desired, the compositions of the invention may contain one or more surfactants. This is particularly desirable when the composition is in the form of an aqueous gel or emulsion.

If present, the surfactant may range from about 0.001 to 50%, preferably from about 0.005 to 40%, more preferably from about 0.01 to 35% by weight of the total composition. Suitable surfactants may be silicone or organic, nonionic, anionic, amphoteric or zwitterionic. Such surfactants include, but are not limited to, those set forth herein.

1. Silicone Surfactants

Suitable silicone surfactants include polyorganosiloxane polymers that have amphiphilic properties, for example contain hydrophilic radicals and lipophilic radicals. These silicone surfactants may be liquids or solids at room temperature.

(a). Dimethicone Copolyols or Alkyl Dimethicone Copolyols

One type of silicone surfactant that may be used is generically referred to as dimethicone copolyol or alkyl dimethicone copolyol. It may be either a water-in-oil or oil-in-water surfactant having an Hydrophile/Lipophile Balance (HLB) ranging from about 2 to 18. Preferably the silicone surfactant is a nonionic surfactant having an HLB ranging from about 2 to 12, preferably about 2 to 10, most preferably about 4 to 6. The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, and mixtures thereof. The term "lipophilic radical" means an organic radical that, when substituted onto the organosiloxane polymer backbone, confers lipophilic properties to the substituted portion of the polymer. Examples of organic radicals that will confer lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof.

One type of suitable silicone surfactant has the general formula:

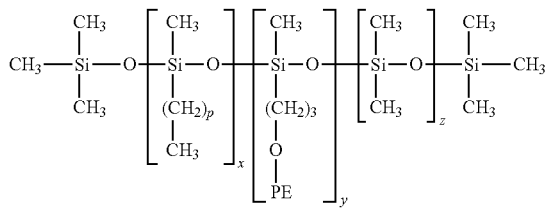

wherein p is 0-40 (the range including all numbers between and subranges such as 2, 3, 4, 13, 14, 15, 16, 17, 18, etc.), and PE is (—$C_2H_4O$)$_a$—(—$C_3H_6O$)$_b$—H wherein a is 0 to 25, b is 0-25 with the proviso that both a and b cannot be 0 simultaneously, x and y are each independently ranging from 0 to 1 million with the proviso that they both cannot be 0 simultaneously. In one preferred embodiment, x, y, z, a, and b are such that the molecular weight of the polymer ranges from about 5,000 to about 500,000, more preferably from about 10,000 to 100,000, and is most preferably approximately about 50,000 and the polymer is generically referred to as dimethicone copolyol.

One type of silicone surfactant is wherein p is such that the long chain alkyl is cetyl or lauryl, and the surfactant is called, generically, cetyl dimethicone copolyol or lauryl dimethicone copolyol respectively.

In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Corning under the tradename 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

(b). Crosslinked Silicone Surfactants

Crosslinked silicone surfactants, often referred to as emulsifying elastomers are suitable. Typically these polyoxyalkylenated silicone elastomers are crosslinked organopolysiloxanes that may be obtained by a crosslinking addition reaction of diorganopolysiloxane comprising at least one hydrogen bonded to silicon and of a polyoxyalkylene comprising at least two ethylenically unsaturated groups. In at least one embodiment, the polyoxyalkylenated crosslinked organopolysiloxanes are obtained by a crosslinking addition reaction of a diorganopolysiloxane comprising at least two hydrogens each bonded to a silicon, and a polyoxyalkylene comprising at least two ethylenically unsaturated groups, optionally in the presence of a platinum catalyst, as described, for example, in U.S. Pat. Nos. 5,236,986 and 5,412,004, 5,837,793 and 5,811,487, the contents of which are incorporated by reference.

Polyoxyalkylenated silicone elastomers that may be used include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

One preferred crosslinked silicone elastomer emulsifier is dimethicone/PEG-10/15 crosspolymer, which provides excellent aesthetics due to its elastomeric backbone, but also surfactancy properties.

2. Organic Nonionic Surfactants

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, Laureth 2-100, formed by the reaction of lauryl alcohol and ethylene oxide where the number of repeating ethylene oxide units is 2 to 100, and so on.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000. Also suitable are ethoxylated propoxylated derivatives of C6-30 saturated or unsaturated fatty acids, for example, Di-PPG-2 myreth-10 adipate, Di-PPG-2 Ceteth-4 adipate, Di-PPG Myristyl Ether Adipate.

Other nonionic surfactants that may be used are formed by the reaction of a carboxylic acid with an alkylene oxide or with a polymeric ether or monomeric, homopolymeric, or block copolymeric ethers; or alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

D. Structuring Agents

It may also be desirable to include one or more structuring agents in the composition. Structuring agents will increase the viscosity, hence structure, the composition. Structuring agents may be lipophilic or hydrophilic, and form part of the aqueous or non-aqueous phase of the composition. If present, the structuring agent may range from about 0.1 to 60%, preferably from about 0.5 to 50%, more preferably from about 1 to 45% of the composition.

Desirable structuring agents include silicone elastomers, silicone gums or waxes, natural or synthetic waxes, polyamides, silicone polyamides and the like.

1. Silicone Elastomers

Silicone elastomers include those that are formed by addition reaction-curing, by reacting an SiH-containing diorganosiloxane and an organopolysiloxane having terminal olefinic unsaturation, or an alpha-omega diene hydrocarbon, in the presence of a platinum metal catalyst. Such elastomers may also be formed by other reaction methods such as condensation-curing organopolysiloxane compositions in the presence of an organotin compound via a dehydrogenation reaction between hydroxyl-terminated diorganopolysiloxane and SiH-containing diorganopolysiloxane or alpha omega diene; or by condensation-curing organopolysiloxane compositions in the presence of an organotin compound or a titanate ester using a condensation reaction between an hydroxyl-terminated diorganopolysiloxane and a hydrolysable organosiloxane; peroxide-curing organopolysiloxane compositions which thermally cure in the presence of an organoperoxide catalyst.

One type of elastomer that may be suitable is prepared by addition reaction-curing an organopolysiloxane having at least 2 lower alkenyl groups in each molecule or an alpha-omega diene; and an organopolysiloxane having at least 2 silicon-bonded hydrogen atoms in each molecule; and a platinum-type catalyst. While the lower alkenyl groups such as vinyl, can be present at any position in the molecule, terminal olefinic unsaturation on one or both molecular terminals is preferred. The molecular structure of this component may be straight chain, branched straight chain, cyclic, or a network. These organopolysiloxanes are exemplified by methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl) polysiloxanes, and dimethylvinylsiloxy-terminated dimethylsiloxane-methyl(3,3,-trifluoropropyl)siloxane copolymers, decadiene, octadiene, heptadiene, hexadiene, pentadiene, or tetradiene, or tridiene.

Curing proceeds by the addition reaction of the silicon-bonded hydrogen atoms in the dimethyl methylhydrogen siloxane, with the siloxane or alpha-omega diene under catalysis using the catalyst mentioned herein. To form a highly crosslinked structure, the methyl hydrogen siloxane must contain at least 2 silicon-bonded hydrogen atoms in each molecule in order to optimize function as a crosslinker.

The catalyst used in the addition reaction of silicon-bonded hydrogen atoms and alkenyl groups, and is concretely exemplified by chloroplatinic acid, possibly dissolved in an alcohol or ketone and this solution optionally aged, chloroplatinic acid-olefin complexes, chloroplatinic acid-alkenylsiloxane complexes, chloroplatinic acid-diketone complexes, platinum black, and carrier-supported platinum.

Examples of suitable silicone elastomers for use in the compositions of the invention may be in the powder form, or dispersed or solubilized in solvents such as volatile or nonvolatile silicones, or silicone compatible vehicles such as paraffinic hydrocarbons or esters. Examples of silicone elastomer powders include vinyl dimethicone/methicone silesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200 which is a fluoro-silicone elastomer, and hybrid silicone powders that contain a phenyl group such as Shin-Etsu's KSP-300, which is a phenyl substituted silicone elastomer; and Dow Corning's DC 9506. Examples of silicone elastomer powders dispersed in a silicone compatible vehicle include dimethicone/vinyl dimethicone crosspolymers supplied by a variety of suppliers including Dow Corning Corporation under the tradenames 9040 or 9041, GE Silicones under the tradename SFE 839, or Shin-Etsu Silicones under the tradenames KSG-15, 16, 18. KSG-15 has the CTFA name cyclopentasiloxane/dimethicone/vinyl dimethicone crosspolymer. KSG-18 has the INCI name phenyl trimethicone/dimethicone/phenyl vinyl dimethicone crosspolymer. Silicone elastomers may also be purchased from Grant Industries under the Gransil trademark. Also suitable are silicone elastomers having long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44. Cross-linked organopolysiloxane elastomers useful in the present invention and processes for making them are further described in U.S. Pat. No. 4,970,252 to Sakuta et al., issued Nov. 13, 1990; U.S. Pat. No. 5,760,116 to Kilgour et al., issued Jun. 2, 1998; U.S. Pat. No. 5,654,362 to Schulz, Jr. et al. issued Aug. 5, 1997; and Japanese Patent Application JP 61-18708, assigned to Pola Kasei Kogyo KK, each of which are herein incorporated by reference in its entirety.

2. Silicone Gums

Silicone gums are also suitable structuring agents. The term "gum" means a silicone polymer having a degree of polymerization sufficient to provide a silicone having a gum-like texture. In certain cases the silicone polymer forming the gum may be crosslinked. The silicone gum typically has a viscosity ranging from about 500,000 to 100 million cst at 25° C., preferably from about 600,000 to 20 million, more preferably from about 600,000 to 12 million cst. All ranges mentioned herein include all subranges, e.g. 550,000; 925,000; 3.5 million.

Such silicone gums may be purchased in pure form from a variety of silicone manufacturers including Wacker-Chemie or Dow Corning, and the like. Such silicone gums include those sold by Wacker-Belsil under the trade names CM3092, Wacker-Belsil 1000, or Wacker-Belsil DM 3096. A silicone gum where X is OH, also referred to as dimethiconol, is available from Dow Corning Corporation under the trade name 1401. The silicone gum may also be purchased in the form of a solution or dispersion in a silicone compatible vehicle such as volatile or nonvolatile silicone. An example of such a mixture may be purchased from Barnet Silicones under the HL-88 tradename, having the INCI name dimethicone.

3. Polyamides or Silicone Polyamides

Also suitable as oil phase structuring agents are various types of polymeric compounds such as polyamides or silicone polyamides.

The term silicone polyamide means a polymer comprised of silicone monomers and monomers containing amide groups as further described herein. The silicone polyamide preferably comprises moieties of the general formula:

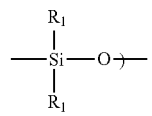

where X is a linear or branched alkylene having from about 1-30 carbon atoms; $R_1$, $R_2$, $R_3$, and $R_4$ are each independently $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

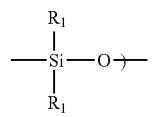

and Y is:

(a) a linear or branched alkylene having from about 1-40 carbon atoms which may be substituted with (i) one or more amide groups having the general formula $R_1CONR_1$, or (ii) $C_{5-6}$ cyclic ring, or (iii) phenylene which may be substituted with one or more $C_{1-10}$ alkyl groups, or (iv) hydroxy, or (v) $C_{3-8}$ cycloalkane, or (vi) $C_{1-20}$ alkyl which may be substituted with one or more hydroxy groups, or (vii) $C_{1-10}$ alkyl amines; or (b) $TR_5R_6R_7$ wherein $R_5$, $R_6$, and $R_7$, are each independently a $C_{1-10}$ linear or branched alkylenes, and T is $CR_8$ wherein $R_8$ is hydrogen, a trivalent atom N, P, or Al, or a $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

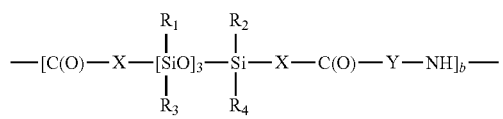

Preferred is where $R_1$, $R_2$, $R_3$, and $R_4$ are $C_{1-10}$, preferably methyl; and X and Y is a linear or branched alkylene. Preferred are silicone polyamides having the general formula:

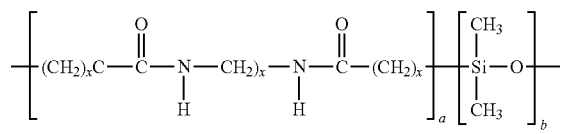

wherein a and b are each independently sufficient to provide a silicone polyamide polymer having a melting point ranging from about 60 to 120° C., and a molecular weight ranging from about 40,000 to 500,000 Daltons. One type of silicone polyamide that may be used in the compositions of the invention may be purchased from Dow Corning Corporation under the tradename Dow Corning 2-8178 gellant which has the CTFA name nylon-611/dimethicone copolymer which is sold in a composition containing PPG-3 myristyl ether.

Also suitable are polyamides such as those purchased from Arizona Chemical under the tradenames Uniclear and Sylvaclear. Such polyamides may be ester terminated or amide terminated. Examples of ester terminated polyamides include, but are not limited to those having the general formula:

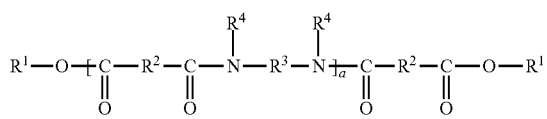

wherein n denotes a number of amide units such that the number of ester groups ranges from about 10% to 50% of the total number of ester and amide groups; each $R_1$ is independently an alkyl or alkenyl group containing at least 4 carbon atoms; each $R_2$ is independently a $C_{4-42}$ hydrocarbon group, with the proviso that at least 50% of the $R_2$ groups are a C30-42 hydrocarbon; each $R_3$ is independently an organic group containing at least 2 carbon atoms, hydrogen atoms and optionally one or more oxygen or nitrogen atoms; and each $R_4$ is independently a hydrogen atom, a $C_{1-10}$ alkyl group or a direct bond to $R_3$ or to another $R_4$, such that the nitrogen atom to which $R_3$ and $R_4$ are both attached forms part of a heterocyclic structure defined by $R_4$—N—$R_3$, with at least 50% of the groups $R_4$ representing a hydrogen atom.

Ester and amide terminated polyamides that may be used include those sold by Arizona Chemical under the tradenames Sylvaclear A200V or A2614V, both having the CTFA name ethylenediamine/hydrogenated dimer dilinoleate copolymer/bis-di-$C_{14-18}$ alkyl amide; Sylvaclear AF1900V; Sylvaclear C75V having the CTFA name bis-stearyl ethylenediamine/neopentyl glycol/stearyl hydrogenated dimer dilinoleate copolymer; Sylvaclear PA1200V having the CTFA name Polyamide-3; Sylvaclear PE400V; Sylvaclear WF1500V; or Uniclear, such as Uniclear 100VG having the INCI name ethylenediamine/stearyl dimer dilinoleate copolymer; or ethylenediamine/stearyl dimer ditallate copolymer. Other examples of suitable polyamides include those sold by Henkel under the Versamid trademark (such as Versamid 930, 744, 1655), or by Olin Mathieson Chemical Corp. under the brand name Onamid S or Onamid C.

4. Natural or Synthetic Organic Waxes

Also suitable as structuring agents may be one or more natural or synthetic waxes such as animal, vegetable, or mineral waxes. Preferably such waxes will have a higher melting point such as from about 60 to 150° C., more preferably from about 65 to 100° C. Examples of such waxes include waxes made by Fischer-Tropsch synthesis, such as polyethylene or synthetic wax; or various vegetable waxes such as bayberry, candelilla, ozokerite, acacia, beeswax, ceresin, cetyl esters, flower wax, citrus wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, grape wax, and polyalkylene glycol derivatives thereof such as PEG6-20 beeswax, or PEG-12 carnauba wax; or fatty acids or fatty alcohols, including esters thereof, such as hydroxystearic acids (for example 12-hydroxy stearic acid), tristearin, tribehenin, oleic acid, stearic acid, and so on.

5. Montmorillonite Minerals

One type of structuring agent that may be used comprises natural or synthetic montmorillonite minerals such as hectorite, bentonite, and quaternized derivatives thereof, which are obtained by reacting the minerals with a quaternary ammonium compound, such as stearalkonium bentonite, hectorites, quaternized hectorites such as Quaternium-18 hectorite, attapulgite, carbonates such as propylene carbonate, bentones, and the like.

6. Silicas and Silicates

Another type of structuring agent that may be used is silica, silicates, or silica silylate, and alkali metal or alkaline earth metal derivatives thereof. These silicas and silicates are generally found in the particulate form and include silica, silica silylate, magnesium aluminum silicate, and the like.

Also suitable as structuring agents are various types of polysaccharides, for example xanthan gum.

E. Sunscreens

It may also be desirable to include one or more sunscreens in the compositions of the invention. Such sunscreens include chemical UVA or UVB sunscreens or physical sunscreens in the particulate form.

1. UVA Chemical Sunscreens

If desired, the composition may comprise one or more UVA sunscreens. The term "UVA sunscreen" means a chemical compound that blocks UV radiation in the wavelength range of about 320 to 400 nm Preferred UVA sunscreens are dibenzoylmethane compounds having the general formula

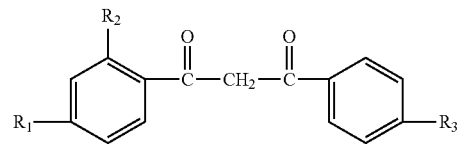

wherein $R_1$ is H, OR and NRR wherein each R is independently H, $C_{1-20}$ straight or branched chain alkyl; $R_2$ is H or OH; and $R_3$ is H, $C_{1-20}$ straight or branched chain alkyl.

Preferred is where $R_1$ is OR where R is a $C_{1-20}$ straight or branched alkyl, preferably methyl; $R_2$ is H; and $R_3$ is a $C_{1-20}$ straight or branched chain alkyl, more preferably, butyl.

Examples of suitable UVA sunscreen compounds of this general formula include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and so on. Particularly preferred is 4-tert-butyl-4'-methoxydibenzoylmethane, also referred to as Avobenzone. Avobenzone is commercial available from Givaudan-Roure under the trademark Parsol 1789, and Merck & Co. under the tradename Eusolex 9020.

Other types of UVA sunscreens include dicamphor sulfonic acid derivatives, such as ecamsule, a sunscreen sold under the trade name Mexoryl™, which is terephthalylidene dicamphor sulfonic acid, having the formula:

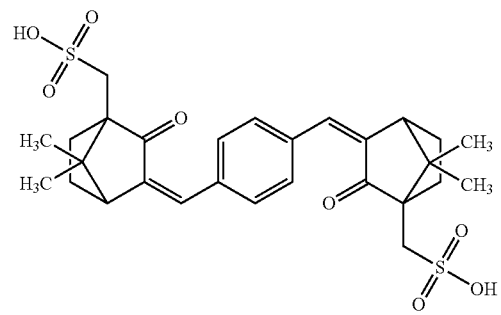 [SMILES: CC1(C)C2CCC1(CS(=O)(=O)O)C(=O)/C2=C\c1ccc(/C=C2\C(=O)C3(CS(=O)(=O)O)CCC2C3(C)C)cc1]

The composition may contain from about 0.001-20%, preferably 0.005-5%, more preferably about 0.005-3% by weight of the composition of UVA sunscreen. In the preferred embodiment of the invention the UVA sunscreen is Avobenzone, and it is present at not greater than about 3% by weight of the total composition.

2. UVB Chemical Sunscreens

The term "UVB sunscreen" means a compound that blocks UV radiation in the wavelength range of from about 290 to 320 nm. A variety of UVB chemical sunscreens exist including alpha-cyano-beta,beta-diphenyl acrylic acid esters as set forth in U.S. Pat. No. 3,215,724, which is hereby incorporated by reference in its entirety. One particular example of an alpha-cyano-beta,beta-diphenyl acrylic acid ester is Octocrylene, which is 2-ethylhexyl 2-cyano-3,3-diphenylacrylate. In certain cases the composition may contain no more than about 110% by weight of the total composition of octocrylene. Suitable amounts range from about 0.001-10% by weight. Octocrylene may be purchased from BASF under the tradename Uvinul N-539.

Other suitable sunscreens include benzylidene camphor derivatives as set forth in U.S. Pat. No. 3,781,417, which is hereby incorporated by reference in its entirety. Such benzylidene camphor derivatives have the general formula:

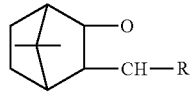

wherein R is p-tolyl or styryl, preferably styryl. Particularly preferred is 4-methylbenzylidene camphor, which is a lipid soluble UVB sunscreen compound sold under the tradename Eusolex 6300 by Merck.

Also suitable are cinnamate derivatives having the general formula:

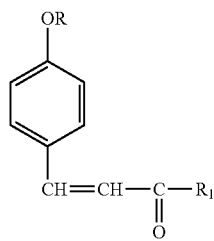

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octoxinate or octyl methoxycinnamate. The compound may be purchased from Givaudan Corporation under the tradename Parsol MCX, or BASF under the tradename Uvinul MC 80. Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at no more than about 3% by weight of the total composition.

Also suitable as UVB screening agents are various benzophenone derivatives having the general formula:

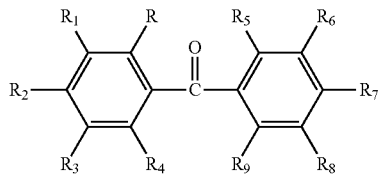

wherein R through $R_9$ are each independently H, OH, $NaO_3S$, $SO_3H$, $SO_3Na$, Cl, R'', OR'' where R'' is $C_{1-20}$ straight or branched chain alkyl Examples of such compounds include Benzophenone 1, 2, 3, 4, 5, 6, 7, 8, 9, 10, 11, and 12. Particularly preferred is where the benzophenone derivative is Benzophenone 3 (also referred to as Oxybenzone), Benzophenone 4 (also referred to as Sulisobenzone), Benzophenone 5 (Sulisobenzone Sodium), and the like. Most preferred is Benzophenone 3.

Also suitable are certain menthyl salicylate derivatives having the general formula:

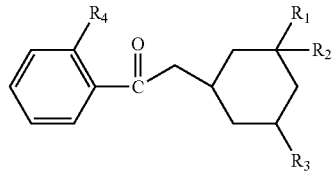

wherein $R_1$, $R_2$, $R_3$, and $R_4$ are each independently H, OH, $NH_2$, or $C_{1-20}$ straight or branched chain alkyl. Particularly preferred is where $R_1$, $R_2$, and $R_3$ are methyl and $R_4$ is hydroxyl or $NH_2$, the compound having the name homomenthyl salicylate (also known as Homosalate) or menthyl anthranilate. Homosalate is available commercially from Merck under the tradename Eusolex HMS and menthyl anthranilate is commercially available from Haarmann & Reimer under the tradename Heliopan. If present, the Homosalate should be found at no more than about 15% by weight of the total composition.

Various amino benzoic acid derivatives are suitable UVB absorbers including those having the general formula:

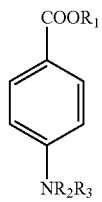

wherein $R_1$, $R_2$, and $R_3$ are each independently H, $C_{1-20}$ straight or branched chain alkyl which may be substituted with one or more hydroxy groups. Particularly preferred is wherein $R_1$ is H or $C_{1-8}$ straight or branched alkyl, and $R_2$ and $R_3$ are H, or $C_{1-8}$ straight or branched chain alkyl. Particularly preferred are PABA, ethyl hexyl dimethyl PABA (Padimate O), ethyldihydroxypropyl PABA, and the like. If present Padimate O should be found at no more than about 8% by weight of the total composition.

Salicylate derivatives are also acceptable UVB absorbers. Such compounds have the general formula: wherein R is a straight or branched chain alkyl, including derivatives of the above compound formed from mono-, di-, or triethanolamines. Particular preferred are octyl salicylate, TEA-salicylate, DEA-salicylate, and mixtures thereof.

Generally, the amount of the UVB chemical sunscreen present may range from about 0.001-45%, preferably 0.005-40%, more preferably about 0.01-35% by weight of the total composition.

If desired, the compositions of the invention may be formulated to have a certain SPF (sun protective factor) values ranging from about 1-100, preferably about from about 10 to 75 with ratios of UVA and UVB ranging from 1-3:1.

F. Film Formers

It may be desired to incorporate one or more film formers into the compositions of the invention. Film formers will generally enhance the film formed by the cosmetic applied to the skin and, in some cases, promote water resistance or transfer resistance. If present, such film formers may range from about 0.1 to 50%, preferably from about 0.5 to 40%, more preferably from about 1 to 35% by weight of the total composition.

Suitable film formers may be based on silicone or organic polymers. Particularly preferred are crosslinked silicone resins generally referred to as MT or MQ resins. Examples of such resins include the MQ resin trimethylsiloxysilicate or an MT resin called polymethylsilsesquioxane. Trimethylsiloxysilicate may be purchased from Dow Corning under the tradename 749 Fluid which is about a 50/50 mixture of trimethylsiloxysilicate and cyclomethicone, or General Electric under the tradename SR1000. Polymethylsilsesquioxane may be purchased from Wacker-Chemie under the tradename MK resin.

The composition may contain other ingredients including preservatives, botanical extracts, vitamins, antioxidants, and the like.

IV. The Method and Product

The invention is directed to a method for imparting color to keratinous surfaces while improving the appearance of dimensionality, depth, or undertones of the surface through application of a composition comprising composite particulates having a portion comprised of at least one colorant and a portion comprised of at least one clear or translucent thermoplastic material to the skin.

It has been found that if at least some portion of the total colorant component present in the composition is replaced with composite particulates, the color applied to skin provides a more natural appearance with depth and dimensionality, while allowing the natural undertones of the skin to show through. The composition may be in the form of foundations, blushes, eyeshadow, and the like. Preferably, when about 0.1-99%, preferably 10-90% of the total colorant component is replaced with composite particulates, optimized coverage and improved appearance will result.

The invention is also directed to a method for reducing the ashy, chalky, or mask-like appearance of a cosmetic composition on skin by applying a composition wherein at least a portion of the total color component has been replaced with composite particulates. Generally when from about 0.1-99%, preferably 10-90% of the total colorant component is replaced with composite particulates the ashy, chalky or mask-like appearance of the composition is reduced when applied to the skin.

The invention is also directed to a method for reducing the number of stock keeping units in a color cosmetic shade range and the resulting color cosmetic shade range. The phrase "color cosmetic" means a composition applied to a keratinous surface such as skin, hair, or nails, for the purpose of imparting color. Examples include foundation makeup, blush, eye shadow, and the like with foundation makeup being most preferred. The term "shade range" means that range of shades offered by the cosmetics manufacturer for one particular SKU of the color cosmetic. By way of example, foundation makeup "Product X" has SKU no. 1234 which identifies Product X, and has 25 different color shades, the shade codes designated by two digit numbers, e.g. 01 through 25, that is, 1234-01, etc. Or in another example, a blush-on "Product Y" is identified by SKU no. 4567 and has six different color shades in the line, the shade codes designated by two digit numbers, e.g. 01 through 06.

In the method of the invention, the number of shades in the shade range for color cosmetics such as foundation makeup, blush-on, and the like may be reduced from 10 to 80% by using the composite particulates to formulate the color cosmetic composition. In formulating the cosmetic compositions, the composite particulates may be substituted for 100% of the total colorant component of the composition. Alternatively, the composite particulates may be substituted for a portion of the colorant component. For example, shade reduction is achieved in the preferred embodiment of the invention when about 30-80%, more preferably from about 40-60% of the total colorant component is replaced with composite particulates. Other suitable ranges may be from about 0.1-99% preferably from about 20-80%, more preferably from about 30-70% by weight of the total colorant component is replaced with composite particulates.

In one embodiment, the method provides for a foundation makeup shade range that exhibits a 10-60% reduction in the number of shades. More particularly, the invention provides for a foundation makeup product line having an original shade range comprised of 15 to 30 individual different shades, wherein the number of shades in the shade range may be reduced from 0.1-99%, preferably from about 10-90% when the foundations are formulated with composite particulates as described herein. In the preferred embodiment as exemplified, the original foundation makeup line had 19 shades. When the foundation formula was prepared wherein from about 40-60% of the total colorant component was replaced with composite particulates, it was possible to reduce the number of shades to 11 and still match all of the skin colors in the same shades as were matched with the 19 shades, thus a reduction of 42% in the number of shades.

The invention will be further described in connection with the following examples which are set forth for the purposes of illustration only.

EXAMPLE 1

A color blend was made by first mixing 50/50 ratio of 250 grams of spherical Polymethylmethacrylate (PMMA) particles (Microsphere M-100, Tomen America; or Sepimat P from SEPPIC) and 250 grams red iron oxide (Unipure Red LC 381EM, Sensient Technologies, South Plainfield, N.J.) at room temperature in a lab scale CBM mixing container (Model Labmaster HC-1A, Teledyne Special Equipment, Readco Products, York, Pa.) having a rotating blade or impellor that spins at about 7,000 rpm with a tumble speed set at 35 rpm and at a process run time of 2 minutes. At room temperature under a fume hood, 250 grams of the color was added to a stainless steel beaker and diluted with 625 grams of acetone with propeller agitation suitable for mixing without splashing. The mixture was allowed to remain in the beaker until it formed a consistency of pourable thick syrup, about 3 to 5 minutes. The beaker contents were poured into a Pyrex-type glass baking dish and spread to a uniform thickness of about 0.25 to 0.5 inches. The mixture was allowed to dry for 24-36 hours or until the color blend was hard and brittle and free from acetone odor.

The dried color blend was removed as a single sheet from the glass dish and broken up into smaller pieces with gloved hands to a size suitable for hammer milling through a 0.20 inch screen.

The color blend pieces were then passed through a hammer mill (Retsch Corporation, Model SR300, Haan Germany) with 0.02 inch screen so that the pieces were reduced to reduce to a particle size suitable for jet milling (generally about 600 microns or less).

The color blend particles were then jet milled using a Model 4 jet mill supplied by Sturtevant, Inc., 348 Circuit Street, Hanover, Mass. The air inlet pressure was set at 105 psi and the grinding pressure at 100 psi. The material feed rate was set at 40 grams per minute. The milling was performed at room temperature for 1 hour. After grinding of the color blend particles they were collected for spray drying.

After jet milling the color blend particles were sieved to remove any large particles (e.g. those greater than 45 microns) prior to spray drying using a lab scale model Octagon Ce Digital vibrating sieve machine (Endicotts Limited, Lombard Road, London SW19 England). The color blend particles that passed through the 45 micron sieve were collected for spray drying. The color blend particles that did not pass through the sieve were discarded.

The color blend particles that passed through the sieve were then coated in a spray drying machine (Glatt Model GPCG-1 Spray Drying Unit, Glatt Technologies, Inc.). The unit was loaded with from about 500 grams to 1 kilogram of the color blend particles. The machine was set with the following parameters: Interval Filter Shaker—vibration set at 5 second intervals; Exhaust Air Flap—set at 0.4 bar; Atomization Spray Pressure—set at 2.5 bar; Liquid Spray Flow Rate set at 25 ml per minute. To 500 grams of color blend particles was added 94.09 grams of Dow Corning 7-4404 Fluid (a mixture of about 35-45 parts trisiloxane and about 40-70 parts dimethicone silylate), which was spray dried onto the color blend particles. This yielded a powder blend with about 7% by weight of the coated color blend particles. After completion of spray drying the particles were collected and dried overnight in an oven (Cascade TEK Model VO-2) at a temperature of 70-80° C.

A final sieve step was performed after spray drying to remove agglomerates. The spray dried coated color blend particles were sieved as set forth above through the 45 micron screen. The resulting coated color blend particles were free flowing and had an average particle size of about 10 microns.

The process set forth herein was repeated with yellow iron oxide (Unipure Yellow LC 182 EM, Sensient Cosmetic Technologies), black iron oxide (Unipure Black LC 989 EM, Sensient Cosmetic Technologies), and titanium dioxide (AFDC 200, Kemora Pigments Oy, Finland). The resulting spray dried coated composite yellow iron oxide particles had a particle size of about 15 microns. The resulting spray dried coated color blend black iron oxides had a particle size of about 10.6 microns; the red iron oxide composite particles about 15 microns; and the titanium dioxide composite particles about 15 microns. The composition of the composite particulates was:

| Color | Colorant | % By Weight | Thermo-plastic Material | % By Weight | Coating | % By Weight |
|---|---|---|---|---|---|---|
| White | TiO$_2$ | 46.5 | PMMA | 46.5 | trisiloxane dimethicone silylate | 7 |
| Red | Red iron oxides | 46.5 | PMMA | 46.5 | trisiloxane dimethicone silylate | 7 |
| Black | Black iron oxides | 46.5 | PMMA | 46.5 | trisiloxane dimethicone silylate | 7 |
| Yellow | Yellow iron oxides | 46.5 | PMMA | 46.5 | trisiloxane dimethicone silylate | 7 |

The resulting composite particulates were used to prepare foundation makeup compositions.

EXAMPLE 2

Foundation makeup compositions were made as follows:

| Ingredient | % By Weight Formula 1(M) | Formula 2 |
|---|---|---|
| Cyclopentasiloxane/PEG/PPG-18/18 Dimethicone (90:10) | 5.00 | 5.00 |
| Sorbitan sesquioleate | 0.20 | 0.20 |
| Cyclopentasiloxane | 19.67 | 19.67 |
| PEG-10 Dimethicone | 3.25 | 3.25 |
| Lecithin | 0.001 | 0.001 |
| Pentaerythrityl tetra-di-t-butyl hydroxyhydrocinnamate | 0.05 | 0.05 |
| Titanium dioxide/triethyoxycaprylylsilane | 7.21 | 3.61 |
| Yellow iron oxides/triethoxycaprylylsilane | 2.42 | 1.21 |
| Red iron oxides/triethoxycaprylylsilane | 0.65 | 0.32 |
| Black iron oxides/triethxycaprylylsilane | 0.22 | 0.11 |
| Silica/titanium dioxide/dimethicone | 0.02 | — |
| Titanium dioxide | — | 3.63 |
| Invention composite colorant (yellow iron oxides/red iron oxides, silica/black iron oxides/PMMA/trisiloxane, dimethicone silylate) 14:32:1:71:11 | — | 6.87 |
| Silica/titanium dioxide/dimethicone | — | 0.02 |
| Hydrogenated lecithin | 0.10 | 0.10 |
| Silica/methoxyamodimethicone/ silsesquioxane copolymer | 1.00 | — |
| Titanium dioxide/triethoxycaprylylsilane | 1.04 | 1.04 |
| Trimethylsiloxysilicate | 2.50 | 2.50 |
| Tocopheryl acetate | 0.05 | 0.05 |
| Cyclopentasiloxane/disteardimonium hectorite/propylene carbonate (75/20/5) | 2.25 | |
| Cyclomethicone/dimethicone/PEG-10 crosspolymer (KSG 24) | 2.50 | 2.50 |
| Cyclomethicone/dimethicone crosspolymer | 3.50 | 3.50 |
| Dimethicone/dimethicone/PEG10/15 crosspolymer | 3.50 | 2.50 |
| Ethylhexylmethoxycinnamate | 2.50 | 2.50 |
| Water | QS100 | QS100 |
| Butylene glycol | 3.00 | 4.00 |
| Sorbic acid | 0.20 | 0.20 |
| Phenoxyethanol/chloroxylenol | 1.00 | 1.00 |
| Xanthan gum | 0.20 | 0.20 |
| Laureth-7 | 0.25 | 0.25 |
| Magnesium sulfate | 1.50 | 1.50 |
| Hyaluronic acid (1% aqueous solution) | 2.00 | 2.00 |

The compositions were prepared by combining the water phase and oil phase ingredients and mixing well to emulsify. The resulting foundations were water in oil emulsions.

EXAMPLE 3

Formula 1 and Formula 2 were tested on 30 female panelists as follows:

- ranging in age from 18 to 55 years,
- normal to oily skin types,
- users of department store or prestige brand liquid foundation,
- used the foundation at least five days a week; and
- preferred full to full-to-medium coverage and a natural finish.

A five day unidentified crossover study was performed and at the beginning all of the panelists were shade acceptors of the test shade. The term "unidentified" means that the panelists were not aware of what cosmetics company was conducting the test. The term "crossover" means that the panelists were divided into two groups of 15. The term "acceptors of the test shade" means that each of the panelists found the test shade of the foundation to be acceptable. Each group of 15 tested the first of the test foundations for two days. On day 3 the panelists returned to the test site and were given the second test foundation for the last two days of the study.

The panelists were provided with the foundation of Formula 1 or Formula 2 in a glass jar labeled "foundation", and instructed to apply the foundation daily after their skin care regimen and in place of their usual foundation by blending over the face. Panelists were instructed not to introduce any new products into their makeup or skin care regimen during the test period. Panelists completed a self-administered questionnaire after each two day usage period and direct comparison questions were asked at the conclusion of the study.

Panelists were asked which foundation, Formula 1 or Formula 2 they preferred when compared to the normally used foundation. The results were as follows:

| Comparison | Formula 1 | Formula 2 (invention) |
|---|---|---|
| No. panelists that liked much/somewhat more/same as regularly used foundation | 23 | 22 |
| No. panelists that liked much/somewhat more than regularly used foundation | 10 | 12 |
| No. panelists that liked much more than regularly used foundation | 2 | 4 |
| No. panelists who liked much/somewhat less than regularly used foundation | 7 | 8 |

EXAMPLE 4

Eleven additional foundation makeup compositions according to the invention were made as follows from the composite particulates prepared in Example 1:

| Ingredient | % By Weight |
|---|---|
| Deionized water | QS100 |
| Cyclopentasiloxane | 19.17 |
| Cyclopentasiloxane/PEG/PPG-18/18 dimethicone | 5.00 |
| Total composite Particulates | ** |
| Titanium dioxide/triethoxycaprylylsilane | 4.24 |
| Cyclomethicone/dimethicone crosspolymer | 3.50 |
| PEG-10 dimethicone | 3.25 |
| Butylene glycol | 3.00 |
| Ethylhexyl methoxycinnamate | 2.50 |
| Cyclopentasiloxane/dimethicone/PEG-10 crosspolymer | 3.50 |
| Dimethicone/dimethicone/PEG-10/15 crosspolymer | 2.50 |
| Magnesium sulfate | 1.50 |
| Cyclopentasiloxane/disteardimonium hectorite/propylene carbonate | 1.13 |
| Titanium dioxide/triethoxycaprylylsilane | 1.04 |
| Phenoxyethanol/chloroxylenol | 1.00 |
| Yellow iron oxides/triethoxycaprylylsilane | 0.85 |
| Silica/methoxyamodimethicone/silsesquioxane copolymer | 0.50 |
| Laureth-7 | 0.25 |
| Sorbitan sesquioleate | 0.20 |
| Sorbic acid | 0.20 |
| Xanthan gum | 0.20 |
| Red iron oxides/triethoxycaprylylsilane | 0.13 |
| Hydrogenated lecithin | 0.10 |
| Tocopheryl acetate | 0.05 |
| Pentaerythrityl tetra-di-t-butyl hydroxyhdrocinnamate | 0.05 |
| Black iron oxides/triethoxycaprylylsilane | 0.03 |
| Sodium hyaluronate | 0.02 |
| Silica/titanium dioxide/methicone | 0.02 |
| Phenoxyethanol | 0.02 |

The amount of composite particulates in % by weight of the total formulas SG1-11 were as follows:

|  | SG1 | SG2 | SG3 | SG4 | SG5 | SG6 | SG7 | SG8 | SG9 | SG10 | SG11 |
|---|---|---|---|---|---|---|---|---|---|---|---|
| W | 8.48 | 7.61 | 7.25 | 7.17 | 5.74 | 5.13 | 2.72 | 1.61 | 1.51 | 1.44 | 1.86 |
| B | 0.07 | 0.12 | 2.57 | 0.21 | 0.21 | 0.34 | 0.42 | 1.15 | 1.35 | 2.43 | 2.09 |
| R | 0.26 | 0.34 | 0.48 | 0.49 | 0.69 | 0.98 | 2.56 | 1.68 | 2.08 | 2.56 | 2.34 |
| Y | 1.69 | 2.43 | 0.20 | 2.63 | 3.86 | 4.05 | 4.80 | 6.06 | 5.56 | 4.07 | 4.21 |
| **Total | 10.5 | 10.5 | 10.5 | 10.5 | 10.5 | 10.5 | 10.5 | 10.5 | 10.5 | 10.5 | 10.5 |

Composite particulate: W = white, B = black, R = red, Y = yellow.

EXAMPLE 5

A study with 200 panelists was conducted to determine whether foundation makeup containing the inventive technology provided improved universal shade matching sufficient to match a variety of skin shades in one shade category and thus contribute to SKU reduction.

200 panelists were recruited. A professional makeup artist selected a foundation from the MAC Studio Fix Fluid SPF15 foundation makeup line (commercially available) that matched the skin color of each of the panelists. The shades of the MAC Studio Fix foundation were as follows:

| Shade Category | Shade Numbers of MAC Studio Fix Fluid SPF15 |
|---|---|
| Light | NC15, NW15 |
| Light/Medium | NC20, NW20, NC25, NW25, NC30 |
| Medium | NC35, NC37, NW30, NC40, NC42 |

| Shade Category | Shade Numbers of MAC Studio Fix Fluid SPF15 |
|---|---|
| Medium/Dark | NC44, NW35, NW40, NW43, NC45 |
| Dark | NW45, NC50, NW47 |
| Deep/Dark | NW50, NW55, NC55 |

The ingredient list on the MAC Studio Fix Fluid SPF 15 foundations that were used read as follows:
ACTIVE INGREDIENTS: OCTINOXATE 2.50% [ ] TITANIUM DIOXIDE 1.00%
INGREDIENTS: WATER\AQUA\EAU [ ] CYCLOPENTASILOXANE [ ] PEG-10 DIMETHICONE [ ] BUTYLENE GLYCOL [ ] TRIMETHYLSILOXYSILICATE [ ] DIMETHICONE [ ] MAGNESIUM SULFATE [ ] DIMETHICONE/PEG-10/15 CROSSPOLYMER [ ] LAMINARIA SACCHARINA EXTRACT [ ] ALGAE EXTRACT [ ] TOCOPHERYL ACETATE [ ] SODIUM HYALURONATE [ ] TOCOPHEROL [ ] LECITHIN [ ] HYDROGENATED LECITHIN [ ] XANTHAN GUM [ ] SORBITAN SESQUIOLEATE [ ] METHOXY AMODIMETHICONE/SILSESQUIOXANE COPOLYMER [ ] LAURETH-7 [ ] PEG/PPG-18/18 DIMETHICONE [ ] DISTEARDIMONIUM HECTORITE [ ] SILICA [ ] DIMETHICONE CROSSPOLYMER [ ] TRIETHOXYCAPRYLYLSILANE [ ] PROPYLENE CARBONATE [ ] PENTAERYTHRITYL TETRA-DI-T-BUTYL HYDROXYHYDROCINNAMATE [ ] SORBIC ACID [ ] CHLOROXYLENOL [ ] PHENOXYETHANOL [ ] [+/−TITANIUM DIOXIDE (CI 77891) [ ] IRON OXIDES (CI 77491, CI 77492, CI 77499) [ ] CHROMIUM OXIDE GREENS (CI 77288)]

The shade of the Studio Fix product that most matched the skin of each panelist was selected by the professional makeup artist and applied to each of the panelists. Both the professional makeup artist and panelist agreed that the color applied matched the skin.

The MAC Studio Fix foundation was then removed from the skin of the panelist and the professional makeup artist selected a foundation from SG1 through SG11 shades and applied to each of the panelists. Upon conclusion of the application both the professional makeup artist and the panelist agreed that the foundation applied matched the skin.

The results showed that the foundations in SG1 through SG11 (11 shades) matched all of the skin shades reflected in the entire shade line (19 shades) for the MAC Studio Fix products, thus resulting in a:

| Shade Category | MAC Studio Fix Shades | Matching SG Shades (invention) | Comments |
|---|---|---|---|
| Light | NC15, NW15 | SG1 | The single SG1 shade matched both NC15 and NW15 shades of MAC Studio Fix foundation in the Light shade category. |
| Light Medium | NC20, NW20, NC25, NW25, NC30 | SG2, SG3 | Two shades, SG2 and SG3, matched five shades of MAC Studio Fix foundation in the Light/Medium shade category. SG2 matched NC20, NW20, NC25. SG3 matched NW25, NC30. |
| Medium | NC35, NC37, NW30, NC40, NC42 | SG4, SG5 | Two shades, SG4 and SG5, matched five shades of MAC Studio Fix foundation in the Medium shade category. SG4 matched NC35, NC37, NW30. SG5 matched NC40, NC42. |
| Medium Dark | NC44, NW35, NW40, NW43, NC45 | SG6, SG7 | Two shades, SG6 and SG7, matched five shades of MAC Studio Fix foundation in the Medium/Dark shade category. SG6 matched NC44, NW35, NW40. SG7 matched NW43, NC45. |
| Dark | NW45, NC50, NW47 | SG8, SG9 | Two shades, SG8 and SG9, matched three shades of MAC Studio Fix foundation in the Dark shade category. SG8 matched NW45, NC50. SG9 matched NW45, NW50, NW47. |
| Deep Dark | NW50, NW55, NC55 | SG10, SG11 | Two shades, SG10 and SG11, matched three shades of MAC Studio Fix foundation in the Deep Dark shade category. SG10 matched NW50, NW55. SG11 matched NW50, NW55, NC55. |

The above results are depicted in the FIG. 1 attached hereto, and demonstrate that foundation compositions containing the composite particulates of the invention are significantly more universal in matching foundation shades thus contributing to SKU reduction. In particular, it was possible to reduce the number of shades to 11 from the original 19 by using the composite particulates of the invention for formulate the foundation composition.

EXAMPLE 6

A composite particulate in the collapsed microsphere form was prepared using Expancel 551 DE 20 d 60 (DE 20 stands for average particle size of 20 microns). About 800 grams was placed into a mixing chamber. Acetone in an amount of about 4,000 mL was added under 20 RPM. A gel was formed and about 343 g of ultra fine titanium dioxide (D 50 2 microns) was added to the gel. The combination of titanium dioxide and the gel was mixed until homogeneous. The acetone was removed by heating the combination in a vacuum chamber. The titanium dioxide particles were entrapped in the microspheres and the outer layer of the microsphere over-coated with about 14 percent by weight of a Dow Corning 1107 silicone polymer. The final particle size of the $TiO_2$-entrapping microspheres was measured using a Malvern Particle Size Analyzer, available from Malvern Instrument Scirocco 2000 at Worcestershire, UK and the result was between 5 to 8 microns.

EXAMPLE 7

A composite particulate in the collapsed microsphere form is prepared using Expancel 551 DE 20 d 60 (DE 20 stands for average particle size of 20 microns). About 800 grams is placed into a mixing chamber. Acetone in an amount of about 4,000 mL is added under 20 RPM. A gel is formed and about 343 g of ultra fine titanium dioxide (D 50 2 microns) is added to the gel. The combination of red iron oxides and the gel is mixed until homogeneous. The acetone is removed by heating the combination in a vacuum chamber. The red iron oxide particles are entrapped in the microspheres and the outer layer of the microsphere over-coated with about 14 percent by weight of a Dow Corning 1107 silicone polymer. The final particle size of the TiO$_2$-entrapping microspheres is measured using a Malvern Particle Size Analyzer, available from Malvern Instrument Scirocco 2000 at Worcestershire, UK and the result is between 5 to 8 microns.

EXAMPLE 8

1 kg of spherical PMMA particles (Sepimat P from SEPPIC) and 1 kg red iron oxide (Unipure Red LC 381EM, Sensient Technologies, South Plainfield, N.J.) were put into an anti-static bag (Anti-Static Bags, Champion Plastics, 220 Clifton Blvd, Clifton, N.J.) and placed into a 50 gallon drum that was rotated at 68 rpm on the drum roller (Morse, East Syracuse, N.Y.) for about 1 hour. The blend was removed from the drum and placed in a LittleFord DVT Polyphase Reactor with 5 gallon inner volume (LittleFord Day Inc., Florence, Ky.) and heated to 72° C. while mixing at the tip speed of blades 0.3-0.5 ft/s. In a separate vessel, 1.42 kg ethanol (Reagent alcohol 200 proof anhydrous—Grade ACS, Sigma Aldrich) was heated to 72° C. and added to the LittleFord unit. The gelled material was mixed until uniform by mixing at the tip speed of blades 0.3-0.5 ft/s. The ethanol was removed by vacuum and heating to 75° C. Dry powder was hammer milled with 0.01 inch screen in a Hosokawa Hammermill 1HP (Hosokawa Col, Osaka Japan). To 2 kg of color blend particles was added 376.36 grams of Dow Corning 7-44-4 Cosmetic Fluid (a mixture of about 35-45 parts trisiloxane and about 4-70 parts dimethicone silylate) and mixed in the LittleFord unit until uniform.

The system was treated by heat at 75° C. under vacuum and nitrogen stream until dry. This yielded a powder blend with about 7% by weight of the coated color blend particles. A final hammermill step was performed after drying to remove agglomerates.

The above process above was repeated using yellow iron oxide (Unipure Yellow LC 182 EM, Sensient Cosmetic Technologies), black iron oxide (Unipure Black LC 989 EM, Sensient Cosmetic Technologies) and titanium dioxide (AFDC 200, Kemore Pigments, Oy Finland). The resulting dried yellow iron oxide-containing particles had a particle size of about 8 microns. The resulting dried coated black iron oxide-containing particles had a particle size of about 8 microns. The red iron oxide-containing particles had a particle size of about 8 microns. The composition of the composite particles was as set forth below:

| Composite Particulate Color | Colorant Used | Colorant % By Weight in Composite Particulate | PMMA % By Weight in Composite Particulate | Coating* % By Weight in Composite Particulate |
|---|---|---|---|---|
| White | TiO$_2$ | 46.5 | 46.5 | 7 |
| Red | red iron oxide | 46.5 | 46.5 | 7 |
| Black | black iron oxide | 46.5 | 46.5 | 7 |
| Yellow | yellow iron oxide | 46.5 | 46.5 | 7 |

*Trisiloxane/dimethicone silylate

EXAMPLE 9

A lipstick composition is prepared as follows:

| Ingredient | w/w % |
|---|---|
| Aloe barbadensis extract/mineral oil | 0.50 |
| Trimethylsiloxypheny dimethicone (PDM 1000) | 1.00 |
| Octyldodecyl stearoyl stearate | 3.05 |
| Ceresin wax | 6.50 |
| Petrolatum | 32.05 |
| Hydrogenated vegetable oils | 14.00 |
| Polybutene | 0.25 |
| Ozokerite | 16.25 |
| Ethylhexyl methoxycinnamate | 7.50 |
| Propyl paraben | 0.15 |
| Phenyl trimethicone | 1.00 |
| Bis-diglyceryl polyacyladipate | 2.50 |
| Cetyl esters | QS |
| Ethylhexyl salicylate | 3.50 |
| Tocopheryl acetate | 0.25 |
| Example 8 Pigments | 4.00 |

The composition is prepared by grinding the pigments in a portion of the cetyl esters. The waxes and oils were separately combined with heat and mixed well. The pigment grind was added to the mixture and stirred well. The mixture is poured into molds and allowed to cool to room temperature.

EXAMPLE 10

Powder eyeshadow and blush compositions are prepared as follows:

| | w/w % | |
|---|---|---|
| Ingredient | Shadow | Blush |
| Aluminum hydroxide | 0.003 | |
| Sorbitan sesquioleate | 0.001 | |
| Ascorbyl palmitate | 0.04 | |
| Barium sulfate | 0.0005 | |
| Soybean extract | 2.47 | |
| BHT | 0.70 | 0.05 |
| Lecithin | | 0.0004 |
| Candelilla wax | 5.85 | |
| Carnauba | 1.76 | |
| Castor seed oil | QS | |
| Polyglyceryl-3 beeswax | 3.23 | |
| Simethicone | | 0.05 |
| Dipentaerythrityl hexahydroxystearate | 2.50 | |
| Isodecyl neopentanoate | 0.05 | |
| Caprylic/capric triglycerides | 9.90 | |
| Mica | 4.75 | |
| Oleyl oleate | 6.70 | |
| Octyl palmitate | | 7.00 |
| Polybutene | | QS |
| Hydrogenated polyisobutene | | 30.13 |
| Dextrin palmitate | | 11.00 |
| Ozokerite | 2.35 | |
| Synthetic wax | 4.95 | |

-continued

| Ingredient | w/w % | |
|---|---|---|
| | Shadow | Blush |
| Diisostearyl malate | 8.70 | |
| Bis-diglyceryl polyacyladipate-2 | 1.47 | |
| Polydecene | 2.10 | 0.35 |
| Mica/titanium dioxide | | 0.80 |
| Propyl paraben | | 0.10 |
| Titanium dioxide | 3.10 | |
| Tocopheryl acetate | 0.04 | |
| Iron oxides | 5.11 | |
| FD&C blue no. 1 aluminum lake | 0.10 | 0.002 |
| D&C Red No. 6 | | 0.01 |
| D&C Red No. 7 Calcium Lake | 0.36 | 0.25 |
| Fragrance | | 0.50 |
| Example 8 pigment blend | 1.00 | 1.15 |

The compositions are prepared by grinding the pigments in a portion of the oil. Separately, the oils and waxes were combined with heat and mixed well. The pigment grind is added. The compositions are pressed into pans.

EXAMPLE 11

Oil in water emulsion mascara compositions are prepared as follows:

| Ingredients | w/w % | | |
|---|---|---|---|
| Water | QS100 | QS100 | QS100 |
| Butylene glycol | 5.00 | 3.00 | 3.00 |
| Ethylhexyl glycerin | | | 0.30 |
| Water/acrylates copolymer | | | 10.00 |
| Polyglyceryl-3 diisostearate liquid | 0.50 | | |
| Iron oxides | 6.00 | 3.00 | 3.00 |
| Example 8 pigment blend | 6.00 | 3.00 | 3.00 |
| Kaolin powder | 4.00 | 3.00 | 6.00 |
| Polyisobutene | | | 6.00 |
| Acrylates/octylacrylamide copolymer | | | 5.00 |
| Methyl methacrylate crosspolymer dispersion | 6.00 | 9.00 | |
| Mica | 2.00 | | |
| Mica/Methyl methacrylate crosspolymer | | | 3.00 |
| Silica | | | 1.00 |
| Polyquaternium-10 | 0.70 | | |
| Steareth-100/Disteareth-100 IPDI copolymer viscous liquid | 1.00 | 3.00 | 2.25 |
| Polyimide-1 | | 12.00 | |
| Sodium polystyrene sulfonate (FF polymer) | | 6.00 | |
| Simethicone (liquid) | 0.10 | 0.10 | 0.10 |
| Biosaccharide gum (skin conditioning agent) | 0.10 | | |
| Sodium dehydroacetate | 0.10 | 0.10 | 0.10 |
| Bentonite (thickening agent) | | 1.25 | 1.25 |
| Disodium EDTA (preservative) | 0.10 | 0.10 | 0.10 |
| Hydrogenated castor oil (solid) | 5.00 | | |
| Steareth-2 (solid) | 2.25 | | |
| Steareth-21 (solid) | 0.75 | 3.50 | 3.50 |
| PEG-6 decyltetradeceth-30 | 0.50 | | |
| PEG-40 hydrogenated castor oil (solid) | 0.50 | | |
| Ricinus Communic (Castor) seed oil (Liquid) | 2.00 | | |
| PEG-20 (Solid) | 2.00 | 3.00 | 3.00 |
| PVP | | | 0.50 |
| PTFE | 2.00 | | |
| Polyvinyl alcohol (Film forming polymer) | | 3.00 | 3.00 |
| Nylon 6/silica | 0.50 | | |
| Water/hydrolyzed wheat protein/PVP crosspolymer | 1.00 | | |

-continued

| Ingredients | w/w % | | |
|---|---|---|---|
| Water/hydrolyzed wheat protein | 1.00 | | |
| Water/hydrolyzed wheat protein/cystine bis-PG-propyl silanetriol copolymer (skin conditioning agetnt) | 7.00 | | |
| Water/polyaminopropyl biguanide | 0.20 | 0.10 | 0.05 |
| Water/acrylates copolymer, butylene glycol/sodium laureth sulfate | 5.00 | | |
| Phenoxyethanol/caprylyl glycol/potassium sorbate/water/hexylene glycol | | 0.75 | |
| Phenoxyethanol | | 0.40 | 0.40 |
| Phenoxyethanol/caprylyl glycol/potassium sorbate/water/hexylene glycol | | | 0.85 |
| Aminomethyl propanediol | | | 0.05 |

The composition is prepared by combining the water phase and oil phase ingredients separately, then mixing the phases to emulsify and form a mascara composition.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

What is claimed is:

1. A method for making a composite particulate in fused agglomerate form and which is not a collapsed microsphere having a portion comprised of at least one colorant and a portion comprised of at least one clear or translucent thermoplastic material comprising the steps of:
   (a) combining one or more colorants in particulate form with polymethylmethacrylate (PMMA) in the form of solid spheres;
   (b) adding solvent in an amount sufficient to swell the PMMA and cause the fused agglomerates of colorant and PMMA to form;
   (c) removing the solvent and causing the mixture to dry,
   (d) subjecting the dried mixture to milling to form fused agglomerates having a particle size ranging from 1 to 100 microns.

2. The method of claim 1 wherein the fused agglomerates of (d) are coated with a coating selected from the group consisting of silicone elastomers, silicone resins, silicone gums, synthetic or natural waxes and mixtures thereof.

3. The method of claim 2 wherein the coated fused agglomerates are sieved to remove particles larger than 45 microns.

4. The method of claim 1 wherein the solvent has a Hildebrand Solubility Parameter ranging from about 1 to 16 (calories/cm$^3$)$^{1/2}$.

5. The method of claim 4 wherein the solvent is acetone, xylene, methylethyl ketone (MEK), dimethylformamide, dimethylchloride, trichloroethylene, trichloromethane, methanol, ethanol, isopropanol, ethyl acetate, butyl acetate, toluene, benzene, cyclohexane, amyl acetate, carbon tetrachloride, toluene, tetrahydrofuran, benzene, diacetone alcohol, ethylene dichloride, methylene chloride, DMSO, morpholine, cellosolve, pyridine, propanol; or $C_{1-4}$ mono- or dialkyl ethers of ethylene glycol, or mixtures thereof.

6. The method of claim 5 wherein the solvent is ethanol.

7. The method of claim 1 wherein (a) 50 parts of colorant is combined with 50 parts PMMA.

8. The method of claim 7 wherein (b) 50 parts of solvent is added.

9. The method of claim 8 wherein the mixture of 50 parts colorant and 50 parts PMMA is exposed to 50 parts solvent for 1 to 10 hours.

10. The method of claim 1 wherein the colorant comprises a mixture of pigments and powders.

* * * * *